(12) United States Patent
Guy et al.

(10) Patent No.: US 12,383,567 B2
(45) Date of Patent: Aug. 12, 2025

(54) USE OF CANNABINOIDS IN THE TREATMENT OF EPILEPSY

(71) Applicant: Jazz Pharmaceuticals Research UK Limited, Sittingbourne (GB)

(72) Inventors: Geoffrey Guy, Cambridge (GB); Volker Knappertz, Cambridge (GB)

(73) Assignee: Jazz Pharmaceuticals Research UK Limited, Sittingbourne (GB)

( * ) Notice: Subject to any disclaimer, the term of this patent is extended or adjusted under 35 U.S.C. 154(b) by 468 days.

(21) Appl. No.: 16/768,241

(22) PCT Filed: Nov. 30, 2018

(86) PCT No.: PCT/GB2018/053483
§ 371 (c)(1),
(2) Date: May 29, 2020

(87) PCT Pub. No.: WO2019/106386
PCT Pub. Date: Jun. 6, 2019

(65) Prior Publication Data
US 2021/0177773 A1 Jun. 17, 2021

(30) Foreign Application Priority Data
Dec. 1, 2017 (GB) .................................... 1720020

(51) Int. Cl.
| | | |
|---|---|---|
| *A61K 31/05* | (2006.01) | |
| *A61K 31/00* | (2006.01) | |
| *A61K 36/185* | (2006.01) | |
| *A61P 25/10* | (2006.01) | |
| *A61P 25/12* | (2006.01) | |
| *A61K 31/436* | (2006.01) | |

(52) U.S. Cl.
CPC .......... *A61K 31/658* (2023.05); *A61K 36/185* (2013.01); *A61P 25/10* (2018.01); *A61P 25/12* (2018.01); *A61K 31/436* (2013.01)

(58) Field of Classification Search
CPC ...... A61K 31/05; A61K 31/436; A61K 31/02; A61K 2300/00
See application file for complete search history.

(56) References Cited

U.S. PATENT DOCUMENTS

| | | |
|---|---|---|
| 2,304,669 A | 12/1942 | Adams |
| 6,383,513 B1 | 5/2002 | Watts et al. |
| 6,403,126 B1 | 6/2002 | Webster |
| 6,949,582 B1 | 9/2005 | Wallace |
| 7,025,992 B2 | 4/2006 | Whittle et al. |
| 8,222,292 B2 | 7/2012 | Goskonda et al. |
| 8,293,786 B2 | 10/2012 | Stinchcomb |
| 8,603,515 B2 | 12/2013 | Whittle |
| 8,632,825 B2 | 1/2014 | Velasco Diez et al. |
| 8,673,368 B2 | 3/2014 | Guy et al. |
| 8,790,719 B2 | 7/2014 | Parolaro et al. |
| 9,017,737 B2 | 4/2015 | Kikuchi et al. |
| 9,023,322 B2 | 5/2015 | Van Damme et al. |
| 9,066,920 B2 | 6/2015 | Whalley et al. |
| 9,095,554 B2 | 8/2015 | Lewis et al. |
| 9,095,555 B2 | 8/2015 | Winnicki |
| 9,125,859 B2 | 9/2015 | Whalley et al. |
| 9,168,278 B2 | 10/2015 | Guy et al. |
| 9,259,449 B2 | 2/2016 | Raderman |
| 9,474,726 B2 | 10/2016 | Guy et al. |
| 9,477,019 B2 | 10/2016 | Li et al. |
| 9,492,438 B2 | 11/2016 | Pollard |
| 9,522,123 B2 | 12/2016 | Whalley et al. |
| 9,630,941 B2 | 4/2017 | Elsohly et al. |
| 9,675,654 B2 | 6/2017 | Parolaro et al. |
| 9,680,796 B2 | 6/2017 | Miller et al. |
| 9,730,911 B2 | 8/2017 | Verzura et al. |

(Continued)

FOREIGN PATENT DOCUMENTS

| | | |
|---|---|---|
| CA | 2 737 447 A1 | 10/2012 |
| CA | 2 859 934 A1 | 3/2016 |

(Continued)

OTHER PUBLICATIONS

Shih et al. Epilepsy & Behavior 2017, 69, 186-222 (Year: 2017).*
Hauser et al. Case Reports in Transplantation, vol. 2016, Article ID 4028492, pp. 1-3 (Year: 2016).*
Yamaori et al. Life Sciences 2011, 88, 730-736 (Year: 2011).*
Iwasaki, K. Drug Metab. Parmacokinet. 2007, 22, 328-335 (Year: 2007).*
Christians et al. Expert Opin. Drug Metab. Toxicol. 2011, 7, 175-200 (Year: 2011).*
Liu et al. World J. Gastroenterol 2009, 15, 3931-3936 (Year: 2009).*
Racha et al. Drug Metab. Pharmacokin. 2003, 18, 128-138 (Year: 2003).*

(Continued)

*Primary Examiner* — Matthew P Coughlin
(74) *Attorney, Agent, or Firm* — COOLEY LLP

(57) ABSTRACT

The present invention relates to the use of cannabidiol (CBD) in the treatment of patients with childhood-onset epilepsy who are concurrently taking immunosuppressant drugs. In particular the immunosuppressant drug is a calcineurin inhibitor. More particularly the immunosuppressant drug is tacrolimus. Where the CBD is used in combination with an immunosuppressant drug, caution should be taken. For example, the dose of either the CBD and/or the immunosuppressant drug may be required to be reduced. Moreover, the patient may need to be monitored for side effects of said drug-drug interaction. Preferably the CBD used is in the form of a highly purified extract of cannabis such that the CBD is present at greater than 98% of the total extract (w/w) and the other components of the extract are characterised. In particular the cannabinoid tetrahydrocannabinol (THC) has been substantially removed, to a level of not more than 0.15% (w/w) and the propyl analogue of CBD, cannabidivarin, (CBDV) is present in amounts of up to 1%. Alternatively, the CBD may be a synthetically produced CBD.

12 Claims, 2 Drawing Sheets

(56) References Cited

U.S. PATENT DOCUMENTS

| | | |
|---|---|---|
| 9,949,936 B2 | 4/2018 | Guy et al. |
| 9,949,937 B2 | 4/2018 | Guy et al. |
| 9,956,183 B2 | 5/2018 | Guy et al. |
| 9,956,184 B2 | 5/2018 | Guy et al. |
| 9,956,185 B2 | 5/2018 | Guy et al. |
| 9,956,186 B2 | 5/2018 | Guy et al. |
| 9,962,341 B2 | 5/2018 | Stott et al. |
| 10,039,724 B2 | 8/2018 | Stott et al. |
| 10,092,525 B2 | 10/2018 | Guy et al. |
| 10,098,867 B2 | 10/2018 | Javid et al. |
| 10,111,840 B2 | 10/2018 | Guy et al. |
| 10,137,095 B2 | 11/2018 | Guy et al. |
| 10,220,005 B2 | 3/2019 | Martinez-Orgado |
| 10,226,433 B2 | 3/2019 | DiMarzo et al. |
| 10,583,096 B2 | 3/2020 | Guy et al. |
| 10,603,288 B2 | 3/2020 | Guy et al. |
| 10,653,641 B2 | 5/2020 | Robson et al. |
| 10,709,671 B2 | 7/2020 | Guy et al. |
| 10,709,673 B2 | 7/2020 | Guy et al. |
| 10,709,674 B2 | 7/2020 | Guy et al. |
| 10,729,665 B2 | 8/2020 | Whalley et al. |
| 10,758,514 B2 | 9/2020 | Liu et al. |
| 10,765,643 B2 | 9/2020 | Guy et al. |
| 10,799,467 B2 | 10/2020 | Whalley et al. |
| 10,807,777 B2 | 10/2020 | Whittle |
| 10,849,860 B2 | 12/2020 | Guy et al. |
| 10,918,608 B2 | 2/2021 | Guy et al. |
| 10,925,525 B2 | 2/2021 | Nakaji |
| 10,966,939 B2 | 4/2021 | Guy et al. |
| 11,000,486 B2 | 5/2021 | Liu et al. |
| 11,065,209 B2 | 7/2021 | Guy et al. |
| 11,065,227 B2 | 7/2021 | Stott et al. |
| 11,096,905 B2 | 8/2021 | Guy et al. |
| 11,147,776 B2 | 10/2021 | Stott et al. |
| 11,147,783 B2 | 10/2021 | Stott et al. |
| 11,154,516 B2 | 10/2021 | Guy et al. |
| 11,154,517 B2 | 10/2021 | Guy et al. |
| 11,160,757 B1 | 11/2021 | Wilkhu et al. |
| 11,160,795 B2 | 11/2021 | Guy et al. |
| 11,207,292 B2 | 12/2021 | Guy et al. |
| 11,224,600 B2 | 1/2022 | Vangara et al. |
| 11,229,612 B2 | 1/2022 | Wright et al. |
| 11,291,631 B2 | 4/2022 | Shah |
| 11,311,498 B2 | 4/2022 | Guy et al. |
| 11,318,109 B2 | 5/2022 | Whalley et al. |
| 11,331,279 B2 | 5/2022 | Vangara et al. |
| 11,357,741 B2 | 6/2022 | Guy et al. |
| 11,400,055 B2 | 8/2022 | Guy et al. |
| 11,406,623 B2 | 8/2022 | Guy et al. |
| 11,413,266 B2 | 8/2022 | Biro et al. |
| 11,419,829 B2 | 8/2022 | Whalley et al. |
| 11,426,362 B2 | 8/2022 | Wright et al. |
| 11,446,258 B2 | 9/2022 | Guy et al. |
| 11,590,087 B2 | 2/2023 | Guy et al. |
| 11,633,369 B2 | 4/2023 | Guy et al. |
| 11,679,087 B2 | 6/2023 | Guy et al. |
| 11,684,598 B2 | 6/2023 | Stott et al. |
| 11,701,330 B2 | 7/2023 | Guy et al. |
| 11,709,671 B2 | 7/2023 | Joubert et al. |
| 11,766,411 B2 | 9/2023 | Guy et al. |
| 11,793,770 B2 | 10/2023 | Stott et al. |
| 11,806,319 B2 | 11/2023 | Wilkhu et al. |
| 11,865,102 B2 | 1/2024 | Guy et al. |
| 11,963,937 B2 | 4/2024 | Guy et al. |
| 12,023,305 B2 | 7/2024 | Whalley et al. |
| 12,064,399 B2 | 8/2024 | Guy et al. |
| 2004/0034108 A1 | 2/2004 | Whittle |
| 2004/0049059 A1 | 3/2004 | Mueller |
| 2004/0110828 A1 | 6/2004 | Chowdhury et al. |
| 2004/0147767 A1 | 7/2004 | Whittle et al. |
| 2005/0042172 A1 | 2/2005 | Whittle |
| 2005/0266108 A1 | 12/2005 | Flockhart et al. |
| 2006/0039959 A1 | 2/2006 | Wessling |
| 2006/0167283 A1 | 7/2006 | Flockhart et al. |
| 2007/0060638 A1 | 3/2007 | Olmstead |
| 2007/0099987 A1 | 5/2007 | Weiss et al. |
| 2007/0238786 A1 | 10/2007 | Hobden et al. |
| 2008/0112895 A1 | 5/2008 | Kottayil et al. |
| 2008/0119544 A1 | 5/2008 | Guy et al. |
| 2008/0188461 A1 | 8/2008 | Guan |
| 2009/0036523 A1 | 2/2009 | Stinchcomb et al. |
| 2009/0264063 A1 | 10/2009 | Tinsley et al. |
| 2009/0306221 A1 | 12/2009 | Guy et al. |
| 2010/0239693 A1 | 9/2010 | Guy et al. |
| 2010/0273895 A1 | 10/2010 | Stinchcomb et al. |
| 2010/0317729 A1 | 12/2010 | Guy et al. |
| 2011/0028431 A1 | 2/2011 | Zerbe et al. |
| 2011/0033529 A1 | 2/2011 | Samantaray et al. |
| 2011/0038958 A1 | 2/2011 | Kikuchi et al. |
| 2011/0082195 A1 | 4/2011 | Guy et al. |
| 2011/0150825 A1 | 6/2011 | Buggy et al. |
| 2012/0004251 A1 | 1/2012 | Whalley et al. |
| 2012/0165402 A1 | 6/2012 | Whalley et al. |
| 2012/0183606 A1 | 7/2012 | Bender et al. |
| 2012/0202891 A1 | 8/2012 | Stinchcomb et al. |
| 2012/0270845 A1 | 10/2012 | Bannister |
| 2013/0143894 A1 | 6/2013 | Bergstrom et al. |
| 2013/0209483 A1 | 8/2013 | McAllister |
| 2013/0245110 A1 | 9/2013 | Guy et al. |
| 2013/0296398 A1 | 11/2013 | Whalley et al. |
| 2014/0100269 A1 | 4/2014 | Goskonda et al. |
| 2014/0155456 A9 | 6/2014 | Whalley et al. |
| 2014/0243405 A1 | 8/2014 | Whalley et al. |
| 2014/0335208 A1 | 11/2014 | Cawthorne et al. |
| 2014/0343044 A1 | 11/2014 | Ceulemens |
| 2015/0111939 A1 | 4/2015 | Gruening et al. |
| 2015/0181924 A1 | 7/2015 | Llamas |
| 2015/0320698 A1 | 11/2015 | Whalley et al. |
| 2015/0335590 A1 | 11/2015 | Whalley et al. |
| 2015/0342902 A1 | 12/2015 | Vangara et al. |
| 2015/0343071 A1 | 12/2015 | Vangara |
| 2015/0359755 A1* | 12/2015 | Guy ............... A61K 31/35 514/94 |
| 2015/0359756 A1 | 12/2015 | Guy et al. |
| 2016/0010126 A1 | 1/2016 | Poulos et al. |
| 2016/0166498 A1 | 6/2016 | Anastassov |
| 2016/0166514 A1 | 6/2016 | Guy et al. |
| 2016/0166515 A1 | 6/2016 | Guy et al. |
| 2016/0220529 A1 | 8/2016 | Guy et al. |
| 2016/0256411 A1 | 9/2016 | Aung-Din |
| 2016/0317468 A1 | 11/2016 | Sankar et al. |
| 2016/0338974 A1 | 11/2016 | Aung-Din |
| 2017/0007551 A1 | 1/2017 | Guy et al. |
| 2017/0008868 A1 | 1/2017 | Dialer et al. |
| 2017/0172939 A1 | 6/2017 | Guy et al. |
| 2017/0172940 A1 | 6/2017 | Guy et al. |
| 2017/0172941 A1 | 6/2017 | Guy et al. |
| 2017/0173043 A1 | 6/2017 | Guy et al. |
| 2017/0173044 A1 | 6/2017 | Guy et al. |
| 2017/0181982 A1 | 6/2017 | Guy et al. |
| 2017/0224634 A1 | 8/2017 | Vangara et al. |
| 2017/0231923 A1 | 8/2017 | Guy et al. |
| 2017/0239193 A1 | 8/2017 | Guy et al. |
| 2017/0246121 A1 | 8/2017 | Guy et al. |
| 2017/0266126 A1 | 9/2017 | Guy et al. |
| 2017/0273913 A1 | 9/2017 | Guy et al. |
| 2018/0028489 A1 | 2/2018 | Vangara et al. |
| 2018/0071210 A1 | 3/2018 | Wilkhu et al. |
| 2018/0228751 A1 | 8/2018 | Stott et al. |
| 2018/0338931 A1 | 11/2018 | Guy et al. |
| 2019/0031601 A1 | 1/2019 | ElSohly et al. |
| 2019/0083418 A1 | 3/2019 | Guy et al. |
| 2019/0091171 A1 | 3/2019 | Guy et al. |
| 2019/0160393 A1 | 5/2019 | Marshall et al. |
| 2019/0167583 A1 | 6/2019 | Shah |
| 2019/0175547 A1 | 6/2019 | Stott et al. |
| 2019/0247324 A1 | 8/2019 | Whalley et al. |
| 2019/0314296 A1 | 10/2019 | Wright et al. |
| 2019/0321307 A1 | 10/2019 | Guy et al. |
| 2019/0365667 A1 | 12/2019 | Wright et al. |
| 2020/0000741 A1 | 1/2020 | Guy et al. |
| 2020/0069608 A1 | 3/2020 | Guy et al. |
| 2020/0138738 A1 | 5/2020 | Guy et al. |
| 2020/0179303 A1 | 6/2020 | Guy et al. |

(56) References Cited

U.S. PATENT DOCUMENTS

| | | |
|---|---|---|
| 2020/0206152 A1 | 7/2020 | Stott et al. |
| 2020/0206153 A1 | 7/2020 | Whalley et al. |
| 2020/0237683 A1 | 7/2020 | Whalley et al. |
| 2020/0297656 A1 | 9/2020 | Guy et al. |
| 2020/0323792 A1 | 10/2020 | Guy et al. |
| 2020/0352878 A1 | 11/2020 | Guy et al. |
| 2020/0368179 A1 | 11/2020 | Guy et al. |
| 2021/0015789 A1 | 1/2021 | Guy et al. |
| 2021/0052512 A1 | 2/2021 | Guy et al. |
| 2021/0059949 A1 | 3/2021 | Wilkhu et al. |
| 2021/0059960 A1 | 3/2021 | Wilkhu et al. |
| 2021/0059976 A1 | 3/2021 | Wilkhu et al. |
| 2021/0069333 A1 | 3/2021 | Velasco Diez et al. |
| 2021/0093581 A1 | 4/2021 | Guy et al. |
| 2021/0100755 A1 | 4/2021 | Whalley et al. |
| 2021/0145765 A1 | 5/2021 | Guy et al. |
| 2021/0167950 A1 | 6/2021 | Arkko et al. |
| 2021/0169824 A1 | 6/2021 | Guy et al. |
| 2021/0196651 A1 | 7/2021 | Guy et al. |
| 2021/0230145 A1 | 7/2021 | Blankman et al. |
| 2021/0244685 A1 | 8/2021 | Guy et al. |
| 2021/0290565 A1 | 9/2021 | Guy et al. |
| 2021/0308072 A1 | 10/2021 | Wright et al. |
| 2021/0330636 A1 | 10/2021 | Guy et al. |
| 2021/0401771 A1 | 12/2021 | Guy et al. |
| 2022/0000800 A1 | 1/2022 | Guy et al. |
| 2022/0008355 A1 | 1/2022 | Guy et al. |
| 2022/0016048 A1 | 1/2022 | Guy et al. |
| 2022/0023232 A1 | 1/2022 | Guy et al. |
| 2022/0040155 A1 | 2/2022 | Guy et al. |
| 2022/0062197 A1 | 3/2022 | Stott et al. |
| 2022/0062211 A1 | 3/2022 | Stott et al. |
| 2022/0087951 A1 | 3/2022 | Guy et al. |
| 2022/0096397 A1 | 3/2022 | Wright et al. |
| 2022/0168266 A1 | 6/2022 | Guy et al. |
| 2022/0183997 A1 | 6/2022 | Guy et al. |
| 2022/0184000 A1 | 6/2022 | Guy et al. |
| 2022/0202738 A1 | 6/2022 | Guy et al. |
| 2022/0211629 A1 | 7/2022 | Wilkhu et al. |
| 2022/0226257 A1 | 7/2022 | Guy et al. |
| 2022/0233495 A1 | 7/2022 | Silcock et al. |
| 2022/0249396 A1 | 8/2022 | Guy et al. |
| 2022/0257529 A1 | 8/2022 | Guy et al. |
| 2022/0265573 A1 | 8/2022 | Guy et al. |
| 2022/0288055 A1 | 9/2022 | Silcock et al. |
| 2022/0323375 A1 | 10/2022 | Guy et al. |
| 2022/0362149 A1 | 11/2022 | Shah |
| 2022/0378714 A1 | 12/2022 | Guy et al. |
| 2022/0378715 A1 | 12/2022 | Guy et al. |
| 2022/0378717 A1 | 12/2022 | Guy et al. |
| 2022/0378738 A1 | 12/2022 | Guy et al. |
| 2022/0387347 A1 | 12/2022 | Whalley et al. |
| 2022/0395470 A1 | 12/2022 | Whalley et al. |
| 2022/0395471 A1 | 12/2022 | Guy et al. |
| 2023/0000789 A1 | 1/2023 | Guy et al. |
| 2023/0022487 A1 | 1/2023 | Guy et al. |
| 2023/0024312 A1 | 1/2023 | Whalley et al. |
| 2023/0026079 A1 | 1/2023 | Guy et al. |
| 2023/0032502 A1 | 2/2023 | Guy et al. |
| 2023/0038423 A1 | 2/2023 | Silcock et al. |
| 2023/0068885 A1 | 3/2023 | Guy et al. |
| 2023/0143812 A1 | 5/2023 | Knappertz et al. |
| 2023/0235825 A1 | 7/2023 | Thompson et al. |
| 2023/0248664 A1 | 8/2023 | Guy et al. |
| 2023/0263744 A1 | 8/2023 | Guy et al. |
| 2023/0277560 A1 | 9/2023 | Checketts et al. |
| 2023/0277561 A1 | 9/2023 | Checketts et al. |
| 2023/0277562 A1 | 9/2023 | Checketts et al. |
| 2023/0277563 A1 | 9/2023 | Checketts et al. |
| 2023/0285419 A1 | 9/2023 | Checketts et al. |
| 2023/0285420 A1 | 9/2023 | Checketts et al. |
| 2023/0285421 A1 | 9/2023 | Checketts et al. |
| 2023/0285422 A1 | 9/2023 | Checketts et al. |
| 2023/0285423 A1 | 9/2023 | Checketts et al. |
| 2023/0285424 A1 | 9/2023 | Checketts et al. |
| 2023/0285425 A1 | 9/2023 | Checketts et al. |
| 2023/0285426 A1 | 9/2023 | Checketts et al. |
| 2023/0285427 A1 | 9/2023 | Checketts et al. |
| 2023/0285428 A1 | 9/2023 | Checketts et al. |
| 2023/0301934 A1 | 9/2023 | Whalley et al. |
| 2023/0301936 A1 | 9/2023 | Guy et al. |
| 2023/0310464 A1 | 10/2023 | Checketts et al. |
| 2023/0346809 A1 | 11/2023 | Craig et al. |
| 2023/0372367 A1 | 11/2023 | Checketts et al. |
| 2023/0372368 A1 | 11/2023 | Checketts et al. |
| 2024/0016819 A1 | 1/2024 | Craig et al. |
| 2024/0025858 A1 | 1/2024 | Silcock et al. |
| 2024/0033229 A1 | 2/2024 | Guy et al. |
| 2024/0043388 A1 | 2/2024 | Silcock et al. |
| 2024/0050452 A1 | 2/2024 | Craig et al. |
| 2024/0091241 A1 | 3/2024 | Guy et al. |
| 2024/0130981 A1 | 4/2024 | Wilkhu et al. |
| 2024/0131041 A1 | 4/2024 | Tse et al. |
| 2024/0165048 A1 | 5/2024 | Guy et al. |
| 2024/0207220 A1 | 6/2024 | Guy et al. |
| 2024/0215910 A1 | 7/2024 | Tse et al. |
| 2024/0226032 A9 | 7/2024 | Wilkhu et al. |
| 2024/0226123 A9 | 7/2024 | Tse et al. |
| 2024/0238218 A1 | 7/2024 | Silcock et al. |
| 2024/0254066 A1 | 8/2024 | Silcock et al. |
| 2024/0254072 A1 | 8/2024 | Silcock et al. |
| 2024/0261234 A1 | 8/2024 | Guy et al. |
| 2024/0293762 A1 | 9/2024 | Loft et al. |

FOREIGN PATENT DOCUMENTS

| | | |
|---|---|---|
| CN | 101040855 A | 9/2007 |
| CN | 103110582 A | 5/2013 |
| CN | 104490873 A | 4/2015 |
| CN | 108 236 608 A | 7/2018 |
| CN | 110 215 443 A | 9/2019 |
| CN | 110 279 617 A | 9/2019 |
| DE | 10 2012 105 063 A1 | 12/2013 |
| EP | 2 311 475 A2 | 4/2011 |
| EP | 2 448 637 B1 | 5/2012 |
| EP | 2 578 561 A1 | 4/2013 |
| EP | 3 157 512 B1 | 5/2018 |
| GB | 2002754 A | 2/1979 |
| GB | 2 377 633 A | 1/2003 |
| GB | 2 380 129 A | 4/2003 |
| GB | 2 381 194 A | 4/2003 |
| GB | 2384707 A | 8/2003 |
| GB | 2434097 A | 7/2007 |
| GB | 2434312 A | 7/2007 |
| GB | 2450753 A | 1/2009 |
| GB | 2456183 A | 7/2009 |
| GB | 2471523 A | 1/2011 |
| GB | 2478595 A | 9/2011 |
| GB | 2479153 A | 10/2011 |
| GB | 2485291 A | 5/2012 |
| GB | 2471565 B | 7/2012 |
| GB | 2478072 B | 12/2012 |
| GB | 2478074 B | 12/2012 |
| GB | 2492487 A | 1/2013 |
| GB | 2487712 A | 10/2015 |
| GB | 2 530 001 A | 3/2016 |
| GB | 2531093 A | 4/2016 |
| GB | 2531278 A | 4/2016 |
| GB | 2531281 A | 4/2016 |
| GB | 2531282 A | 4/2016 |
| GB | 2539472 A | 12/2016 |
| GB | 2 542 155 A | 3/2017 |
| GB | 2438682 A | 12/2017 |
| GB | 2551987 A | 1/2018 |
| GB | 2584140 A | 11/2020 |
| WO | WO 01/95899 A2 | 12/2001 |
| WO | WO 2002/064109 A2 | 8/2002 |
| WO | WO 02/089945 A2 | 11/2002 |
| WO | WO 2003/099302 A1 | 12/2003 |
| WO | WO 2004/016246 A1 | 2/2004 |
| WO | WO 2004/016277 A2 | 2/2004 |
| WO | WO 2004/026802 A1 | 4/2004 |
| WO | WO 2005/120478 A1 | 12/2005 |
| WO | WO 2006/054057 A2 | 5/2006 |

(56) References Cited

FOREIGN PATENT DOCUMENTS

| | | |
|---|---|---|
| WO | WO 2006/017892 A1 | 12/2006 |
| WO | WO 2006/133941 A2 | 12/2006 |
| WO | WO 2007/032962 A2 | 3/2007 |
| WO | WO 2007/052013 A1 | 5/2007 |
| WO | WO 2007/083098 A1 | 7/2007 |
| WO | WO 2007/138322 A1 | 12/2007 |
| WO | WO 2008/019146 A2 | 2/2008 |
| WO | WO 2008/021394 A2 | 2/2008 |
| WO | WO 2008/094181 A3 | 8/2008 |
| WO | WO 2008/129258 A1 | 10/2008 |
| WO | WO 2008/144475 A1 | 11/2008 |
| WO | WO 2008/146006 A1 | 12/2008 |
| WO | WO 2009/007697 A1 | 1/2009 |
| WO | WO 2009/007698 A1 | 1/2009 |
| WO | WO 2009/020666 A1 | 2/2009 |
| WO | WO 2009/093018 A1 | 7/2009 |
| WO | WO 2011/001169 A1 | 1/2011 |
| WO | WO 2011/121351 A1 | 10/2011 |
| WO | WO 2012/033478 A1 | 3/2012 |
| WO | WO 2012/093255 A1 | 7/2012 |
| WO | WO 2012/160358 A1 | 11/2012 |
| WO | WO 2013/032351 A1 | 3/2013 |
| WO | WO 2013/045891 A1 | 4/2013 |
| WO | WO 2014/168131 A1 | 11/2013 |
| WO | WO 2014/108899 A1 | 7/2014 |
| WO | WO 2014/146699 A1 | 9/2014 |
| WO | WO 2015/065544 A1 | 5/2015 |
| WO | WO 2015/142501 A1 | 9/2015 |
| WO | WO 2015/184127 A2 | 12/2015 |
| WO | WO 2015/193667 A1 | 12/2015 |
| WO | WO 2015/193668 A1 | 12/2015 |
| WO | WO 2016/059399 A1 | 4/2016 |
| WO | WO 2016/059403 A1 | 4/2016 |
| WO | WO 2016/059405 A1 | 4/2016 |
| WO | WO 2016/084075 A1 | 6/2016 |
| WO | WO 2015/187988 A1 | 7/2016 |
| WO | WO 2016/118391 A1 | 7/2016 |
| WO | WO 2016/147186 A1 | 9/2016 |
| WO | WO 2016/022936 A1 | 11/2016 |
| WO | WO 2016/176279 A1 | 11/2016 |
| WO | WO 2016/191651 A1 | 12/2016 |
| WO | WO 2016/199148 A1 | 12/2016 |
| WO | WO 2016/203239 A1 | 12/2016 |
| WO | WO 2017/042567 A1 | 3/2017 |
| WO | WO 2017/139496 A1 | 8/2017 |
| WO | WO 2017/168138 A1 | 10/2017 |
| WO | WO 2017/203529 A1 | 11/2017 |
| WO | WO 2017/204986 A1 | 11/2017 |
| WO | WO 2018/002636 A1 | 1/2018 |
| WO | WO 2018/002637 A1 | 1/2018 |
| WO | WO 2018/002665 A1 | 1/2018 |
| WO | WO 2018/011808 A1 | 1/2018 |
| WO | WO 2018/037203 A1 | 3/2018 |
| WO | WO 2018/115962 A1 | 6/2018 |
| WO | WO 2018/200024 A1 | 11/2018 |
| WO | WO 2018/234811 A1 | 12/2018 |
| WO | WO 2019/020738 A1 | 1/2019 |
| WO | WO 2019/097238 A1 | 5/2019 |
| WO | WO 2019/145700 A1 | 8/2019 |
| WO | WO 2019/207319 A1 | 10/2019 |
| WO | WO 2019/210210 A1 | 10/2019 |
| WO | WO 2019/211795 A1 | 11/2019 |
| WO | WO 2020/225540 A1 | 11/2020 |
| WO | WO 2020/234569 A1 | 11/2020 |
| WO | WO 2021/019231 A1 | 2/2021 |

OTHER PUBLICATIONS

Galetin et al. Drug Metabolism and Disposition 2003, 31, 1108-111 (Year: 2003).*
Tang et al. Scientific Reports, 2017, 7:42192 (Year: 2017).*
Ciszek, M. Central European Journal of Urology 2013, 66, 350-351 (Year: 2013).*
Gaber et al. Transplantation 2013, 96, 191-197 (Year: 2013).*
Leino et al. Am. J. Transplant 2019, 19, 2944-2948 (Year: 2019).*
U.S. Appl. No. 14/741,829, filed Jun. 17, 2015.
U.S. Appl. No. 15/519,244, filed Apr. 14, 2017.
U.S. Appl. No. 15/751,563, filed Feb. 9, 2018.
U.S. Appl. No. 16/314,569, filed Dec. 31, 2018.
U.S. Appl. No. 16/314,583, filed Dec. 31, 2018.
U.S. Appl. No. 16/328,209, filed Feb. 25, 2018.
U.S. Appl. No. 16/467,639, filed Jun. 7, 2019.
U.S. Appl. No. 16/486,750, filed Aug. 16, 2019.
U.S. Appl. No. 16/591,702, filed Oct. 3, 2019.
U.S. Appl. No. 16/624,106, filed Dec. 18, 2019.
U.S. Appl. No. 16/651,751, filed Mar. 27, 2020.
U.S. Appl. No. 16/737,707, filed Jan. 8, 2020.
U.S. Appl. No. 16/764,701, filed May 15, 2020.
U.S. Appl. No. 16/791,940, filed Feb. 14, 2020.
U.S. Appl. No. 16/893,018, filed Jun. 4, 2020.
U.S. Appl. No. 16/959,350, filed Jun. 30, 2020.
U.S. Appl. No. 16/959,357, filed Jun. 30, 2020.
U.S. Appl. No. 16/960,665, filed Jul. 8, 2020.
U.S. Appl. No. 16/989,605, filed Aug. 10, 2020.
U.S. Appl. No. 17/011,715, filed Sep. 3, 2020.
U.S. Appl. No. 17/025,130, filed Sep. 18, 2020.
U.S. Appl. No. 17/068,326, filed Oct. 12, 2020.
U.S. Appl. No. 17/119,873, filed Dec. 11, 2020.
U.S. Appl. No. 17/147,005, filed Jan. 12, 2021.
U.S. Appl. No. 17/188,766, filed Mar. 1, 2021.
U.S. Appl. No. 17/198,965, filed Mar. 11, 2021.
U.S. Appl. No. 17/242,075, filed Apr. 27, 2021.
[No Author Listed] Cannabidiol Therapy for Aicardi Syndrome, Aug. 2014, 4 pages.
[No Author Listed], Cannabinoid. Wikipedia. Retrieved on Jul. 9, 2015 from https://en.wikipedia.org/wiki/Cannabinoid, 15 pages.
No Author Listed], "Missouri House passes cannabis extract legislation," Kansas City Star, 2014, https://kansascity.com/news/politics-government/article346747.html, 2 pages.
[No Author Listed], Cover and Table of Contents, J Pharmacology and Exp Therapeutics, Feb. 2010, 332(2), 4 pages.
AFINITOR® (everolimus) tablets, for oral use, and AFINITOR DISPERZ® (everolimus tablets for oral suspension) Prescribing Information, 2009, 49 pages.
Alger, "Not too excited? Thank your endocannabinoids," Neuron, 51(4):393-595 (2006).
Ames et al., "Anticonvulsant effect of cannabidiol," S Afr Med J., 69(1):14 (1986), 1 page.
American Epilepsy Society, "Three Studies Shed New Light on the Effectiveness of Cannabis in Epilepsy," Oct. 14, 2014, 2 pages.
Arain, "Pregabalin in the management of partial epilepsy," Neuropsychiatr Dis Treat., 5:407-413 (2009); Epub Aug. 20, 2009.
Arslan, A. & Tirnaksiz, F., "Self-emulsifying Drug Delivery Systems," F ABAD J Pharm Sci, 38(1):55-64 (2013).
Arimanoglou et al., "All children who experience epileptic falls do not necessarily have Lennox-Gastaut syndrome . . . but many do," Epileptic Discord, 13:S3-S13 (2011).
Avoli et al., "Cellular and molecular mechanisms of epilepsy in the human brain," Prog Neurobiol., 77(3):166-200 (2005).
Bakhsh, "Pregabalin in the management of partial epilepsy," Miftaah-al-Khazaain, 1930:607-608, with English translation, 4 pages.
Bancaud, "Proposal for Revised Clinical and Electroencephalographic Classification of Epileptic Seizures," Epilepsia, 22(4):489-501 (1981).
Banerjee et al., "Case Report: Aicardi syndrome: A report of five Indian cases," Neurology India, 54(1):91-93 (2006).
Barker-Haliski et al. "How Clinical Development Can, and Should Inform Translational Science," Neuron, 84:582-593 (2014).
Benowitz et al. "Metabolic and Psychophysiologic studies of cannabidiol hexobarbital interaction," Clin Pharmacol Ther., 28(1):115-120 (1980).
Bertram, "The Relevance of Kindling for Human Epilepsy," Epilepsia, 48(Suppl. 2):65-74 (2007).
Bhatt, V. P. & Vashishtha, D. P., "Indigenous plants in traditional healthcare system in Kedarnath valley of western Himalaya," Indian J Tradit Knowl., 7(2):300-310 (2000).

(56) References Cited

OTHER PUBLICATIONS

Bhattacharyya et al., "Modulation of mediotemporal and ventrostriatal function in humans by Delta9-tetrahydrocannabinol: a neural basis for the effects of Cannabis sativa on learning and psychosis," Arch Gen Psychiatry, 66(4):442-451 (2009); doi:10.1001/archgenpsychiatry.2009.17.
Bipolar Health Group (Charlotte's Web Hemp Remedy, available online at http:/bipolarhealthgroup.org/index.php/charlottes-web-hemp-remedy/, accessed Sep. 6, 2017, 6 pages.
Booth, "Legalization's opening of medical pot research is dream and nightmare," Denver Post, Dec. 14, 2013, 6 pages.
Bostanci, M. O. & Bagirici, F., "The effects of octanol on penicillin induced epileptiform activity in rats: an in vivo study," Epilepsy Research, 71:188-194 (2006).
Braida, et al., "Post-ischemic treatment with cannabidiol prevents electroencephalographic flattening, hyperlocomotion and neuronal injury in gerbils," Neuroscience Letters., 346:61-64 (2003).
Brown et al., Child Neurology Foundation, "LGS" (Lennox-Gastaut Syndrome), available at http://www.childneurologyfoundation.org/disorders/lgs-lennox-gastaut-syndrome, 2019, 7 pages.
Brust, J. C. M. et al., "Marijuana use and the risk of new onset seizures," Trans Am Clin Climatol Assoc., 103:176-181 (1992).
Carlini et al., "Hypnotic and antiepileptic effects of cannabidiol," J Clin Pharmacol., 21:417S-427S (1981).
Charlotte's Web [online], "When to expect Results from CW Hemp Oil," Mar. 13, 2017, retrieved on May 21, 2018, URL https://www.cwhemp.com/blog/expecting-results-from-hemp, 6 pages.
Charlotte's Web [online], "Whole-Plant Phyto-Cannabinoids Outperform Single Molecular Compounds," Charlotte's Web Stanley Brothers, URL https://www.charlottesweb.com/blog/whole-plant-cw-hemp-cannabinoids, Dec. 18, 2019, 3 pages.
Castel-Branco et al. "The Maximal Electroshock Seizure (MES) Model in the Preclinical 98. Assessment of Potential New Anti epileptic Drugs," Methods Find Exp Clin Pharmacol., 31 (2); 101-106, 2009.
ChildNeurologyFoundation.org [online], "Disorder Directory: Learn from the Experts—LGS (Lennon-Gastaut Syndrome)," Child Neurology Foundation, available on or before Sep. 6, 2015, retrieved on May 21, 2018; URL http://www.childneurologyfoundation.org/disorders/lgs-Lennox-gastaut-syndrome, 10 pages.
2 to 20 years: Girls Stature-for-age and Weight-for-age percentiles; www.cdc.growthcharts, May 30, 2000 (accessed Apr. 11, 2019), 2019, 1 page.
Chiron, C. & Dulac, O., "The Pharmacologic Treatment of Dravet Syndrome," Epilepsia, 52 (Suppl. 2):72-75 (2011).
Chiu, P. et al., "The Influence of Cannabidiol and A-Tetrahydrocannabinol on Cobalt Epilepsy in Rats," Epilepsia, 20:365-375 (1979).
Chou, "Theoretical basis, experimental design, and computerized simulation of synergism and antagonism in drug combination studies," Pharmacol Rev., 58(3):621-681 (2006).
Clinical trials.gov [online], Identifier: NCT02544750, "An open-label Extension Trial of Cannabidiol (GWP42003-P, CBD) for Seizures in Tuberous Sclerosis Complex (GWPCARE6)," Sponsor: GW Research Ltd, U.S. National Library of Medicine, Oct. 1, 2018; Retrieved from https://clinicaltrials.gov/ct2/show/NCT02544750, 6 pages.
Clinical Drug Interaction Studies—Cytochrome P450 Enzyme- and Transporter-Mediated Drug Interactions Guidance for Industry, U.S. Department of Health and Human Services, Food and Drug Administration, Center for Drug Evaluation and Research (CDER), Jan. 2020, 27 pages.
Conry et al., "Clobazam in the treatment of Lennox-Gastaut syndrome," Epilepsia, 50:1158-1166 (2009).
Consroe et al. "Anticonvulsant nature of marihuana smoking," JAMA, 234(3):306-307 (1975).
Consroe et al. "Anticonvulsant drug antagonism of delta9tetrahydrocannabinol-induced seizures in rabbits," Res Commun Chem Pathol Pharmacol., 16(1):1-13 (1977).

Consroe et al. "Anticonvulsant interaction of cannabidiol and ethosuximide in rats," J Pharm Pharmacol., 29(8):500-501 (1977). doi:10.1111/j.2042-7158.1977.tb11378.x.
Consroe, P. & Wolkin, A., "Cannabidiol—antiepileptic drug comparisons and interactions in experimentally induced seizures in rats," J Pharmacol Exp Ther., 201(1):26-32 (1977).
Consroe et al. "Effects of cannabidiol on behavioral seizures caused by convulsant drugs or current in mice," Eur J Pharmacol., 83(3-4):293-298 (1982).
Consroe, P. & Snider, S. R., "Chapter 2. Therapeutic Potential of Cannabinoids in Neurological disorders," Cannabinoids as Therapeutic Agents, R. Mechoulam, Ed., pp. 21-49 (1986).
Consroe et al. Chapter 12, "Potential Role of Cannabinoids for Therapy of Neurological Disorders," in Marijuana Cannabinoids: Neurobiology and Neurophysiology, Ed. L. Murphy (1992), 72 pages.
Cortesi et al. "Potential therapeutical effects of cannabidiol in children with pharmacoresistant epilepsy," Med Hypotheses, 68(4):920-921 2007). Epub Nov. 16, 2006.
Cortez & Snead, "Chapter 10: Pharmacologic Models of Generalized Absence Seizures in Rodents," Models of Seizures and Epilepsy, 111-126 (2006).
Crespel et al., "Lennox-Gastaut Syndrome," Chapter 14, in Epileptic Syndromes in Infancy, Childhood, and Adolescence, 5th Edition, ed. M. Bureau, et al., pp. 189-216.
Cunha et al. "Chronic administration of cannabidiol to healthy volunteers and epileptic patients." Pharmacology, 21(3):175-85 (1980).
Czapinski, et al. "Randomized 36-month comparative study of valproic acid (VPA), phenytoin (PHT), phenobarbital (PB) and carbamazepine (CBZ) efficacy in patients with newly diagnosed epilepsy with partial complex seizures." J Neurolog Sci., 150:S162 (1997).
Dasa et al. "Key Attributes of TKDL: Ganja," Brhat Nighantu Ratnakara (Saligramanighantubhusanam), RS/4336, vol. IV. 1997:170, with English translation, 5 pages.
Davis et al. "Antiepileptic action of marijuana-active substances," Federation Proceedings, 8:284-285 (1949).
Davis et al. "A predominant role for inhibition of the adenylate cyclase/protein kinase A pathway in ERK activation by cannabinoid receptor 1 in NIE-115 neuroblastoma cells." J Biol Chem. 278(49):48973-80 (2003). Epub Sep. 29, 2003.
De Oliveira, et al. "Anticonvulsant activity of β-caryophyllene against pentylenetetrazol-induced seizures." Epilepsy Behav., 56:26-31 (2016). doi: 10.1016/j.yebeh.2015.12.040.
Devinsky et al., "Cannabidiol: Pharmacology and potential therapeutic role in epilepsy and other neuropsychiatric disorders," Epilepsia, 55(6):791-802 (2014).
Dravet, "The core Dravet syndrome phenotype," Epilepsia. 52 Suppl 2:3-9. doi: 10.1111/j. 1528-1167.2011.02994.x. (2011).
Dreifus et al., "Proposal for Revised Clinical and Electroencephalographic Classification of Epileptic Seizures," Epilepsie, 22:489-501 (1981).
Dulac, "Use of Lamotrigine in Lennox-Gastaut and Related Epilepsy Syndromes," J. Child Neurolog, 12(Supplement 1):S23-S29 (1997).
Dulac, "Vigabatrin in Childhood Epilepsy," J. Child Neurolog., 6(Supplement 2), S30-S37 (1991).
Eadie, "Shortcomings in the current treatment of epilepsy," Expert Rev Neurother, 12(12):1419-1427 (2012).
Ebrahimi-Fakhari, D. et al., "Cannabidiol Elevates mTOR Inhibitor Levels In Tuberous Sclerosis Complex Patients," (2020) Pediatric Neurology, 12 pages; https://doi.org/10.1016/j.pediatrneurol.2019.11.017.
Elsohly and Gul. "Constituents of Cannabis Sariva," Chapter 1, Handbook of Cannabis, ed. Roger G. Pertwee, pp. 3-22 (2014).
Ettienne De Meijer, "The Chemical Phenotypes (Chemotypes) of Cannabis," Chapter 5, Handbook of Cannabis, Handbook of Cannabis, Roger G. Pertwee (ed.), pp. 89-110 (2014).
Engel, "Report of the ILAE classification core group," Epilepsia, 47(9):1558-1568 (2006).
Engel, "Chapter 1: What Should be Modeled?" In Models Seizure Epilepsy, 2006, 14 pages.

(56) References Cited

OTHER PUBLICATIONS

Eggers, "Temporal lobe epilepsy is a disease of faulty neuronal resonators rather than oscillators, and all seizures are provoked, usually by stress," Med Hypotheses., 69(6):1284-9 (2007).
EPIDIOLEX® (cannabidiol) oral solution, CV, Prescribing Information, 2018, 30 pages.
Fariello. "Parenteral Penicillin in Rats: An Experimental Model of Multifocal Epilepsy," Epilepsia, 17:217-222 (1976).
Ferdinand, et al., "Cannabis—psychosis pathway independent of other types of psychopathology," Schizophr Res., 79(2-3):289-295 (2005).
Fisher et al., "The impact of epilepsy from the patient's perspective I. Descriptions and subjective perceptions," Epilepsy Res, 41(1):39-51 (2000).
Gabor et al., "Lorazepam versus phenobarbital: Candidates for drug of choice for treatment of status epilepticus," J Epilepsy, 3(1):3-6 (1990).
Galilly et al., "Overcoming the Bell-Shaped Dose-Response of Cannabidiol by Using Cannabis Extract Enriched in Cannabidiol," Pharmacology & Pharmacy, 6:75-85 (2015).
Gardner [online], "Comes Now Epidiolex (FDA Approves IND Studies of CBD)," BeyondTHC.com, Oct. 22, 2013, retrieved on Jan. 31, 2018, URL http://www.beyondthc.com/comes-now-epidiolex-fda-approves-ind-studies-of-cbd, 4 pages.
Gastaut, "Clinical and electroencephalographical classification of epileptic seizures," Epilepsia, 11(1): 102-113 (1970).
Gedde [online], "Clinical Experience with Cannabis in Treatment-Resistant Pediatric Epilepsy," Marijuana for Medical Professionals Conference, Sep. 9-11, 2014, URL <http://www.theroc.us/images/gedde_presentation.pdf, Sep. 9-11, 2014>, 45 pages.
Geffrey et al. "Cannabidiol (CBD) Treatment for Refractory Epilepsy," American Epilepsy Society, Annual Meeting Abstract 2.427, 2014, retrieved on Feb. 10, 2017, URL <https://www.aesnet.org/meetings_events/annual_meeting_abstracts/view/1868979>, 2 pages.
Green, "CBD: An Unconventional Therapy," available online at http://nugs.com/article/cbd-anunconventional-therapy.html, published Mar. 24, 2014, 5 pages.
Gresham et al."Treating Lennox-Gastaut syndrome in epileptic pediatric patients with third generation rufinamide," Neuropsychiatr Dis Treat., 6:639-645, Oct. 5, 2010.
Gross et al. "Marijuana use and epilepsy: prevalence in patients of a tertiary care epilepsy center," Neurology, 62(11):2095-2097 (2004).
Guimaraes et al., "Antianxiety effect of cannabidiol in the elevated plus-maze," Psychopharmacology (Berl.), 62(11):2095-2097 (2004).
Guerrini et al., "Lamotrigine and Seizure Aggravation in Severe Myoclonic Epilepsy," Epilepsia, 39(5):508-512 (1998).
GWPharm [online], "GW Pharmaceuticals Announces Epidiolex(R) Receives Fast Track Designation from FDA for the Treatment of Dravet Syndrome," GW Pharmaceuticals Press Release, Jun. 6, 2014, retrieved on Mar. 1, 2017, URL https://www.gwpharm.com/about-US/news/gw-pharmaceuticals-announces-epidiolex%C2%AE-receives-fast-track-designation-fda-treatment, 2 pages.
GWPharm [online], "GW Pharmaceuticals Announces Physician Reports of Epidiolex(R) Treatment Effect in Children and Young Adults with Treatment-resistant epilepsy from Physician-Led Expanded Access Treatment Program," GW Pharmaceuticals Press Release, Jun. 17, 2014, retrieved on May 1, 2017, URL <https://www.gwpharm.com/about-us/news/gw-pharmaceuticals-announces-physician-reports-epidiolex%C2%AE-treatment-effect-children>, 8 pages.
GWPharm [online], "GW Pharmaceuticals Provides Update on Orphan Program in Childhood Epilepsy for Epidiolex®," GW Pharmaceuticals Press Release, Nov. 15, 2013, retrieved on Jun. 20, 2018, URL <https://www.gwpharm.com/about-us/news/gw-pharmaceuticals-provides-update-orphan-program-childhood-epilepsy-epidiolex%C2%AE>, 5 pages.
GWPharm [online], "GW Pharmaceuticals Receives Orphan Drug Designation by FDA for Epidiolex® in the treatment of Lennox-Gastaut Syndrome," GW Pharmaceuticals Press Release, Feb. 28, 2014, retrieved on Feb. 10, 2017, URL <https://www.gwpharm.com/about-us/news/gw-pharmaceuticals-receives-orphan-drug-designation-fda-epidiolex%C2%AE-treatment-lennox>, 4 pages.
Heinemann et al., "An Overview of in Vitro Seizure Models in Acute and Organotypic Slices," Chapter 4, 35-44 (2006).
Hill et al. "Δ9-Tetrahydrocannabivarin suppresses in vitro epileptiform and in vivo seizure activity in adult rats," Epilepsia, 51(8):1522-1532 (2010); doi: 10.1111/j.1528-1167.2010.02523.x. Epub Feb. 26, 2010.
Hill, "Cannabidivarin-rich cannabis extracts are anticonvulsant in mouse and rat via a CB 1 receptor-independent mechanism," British Journal of Pharmacology, 170(3): 679-692 (2013).
Holmes et al., "Choosing the correct AED: From Animal Studies to the Clinic," Pediatr Neurol., 38(3):151-162 (2008).
Iannotti et al. "Nonpsychotropic plant cannabinoids, cannabidivarin (CBDV) and cannabidiol (CBD), activate and desensitize transient receptor potential vanilloid 1 (TRPV1) channels in vitro: potential for the treatment of neuronal hyperexcitability," ACS Chem Neurosci., 5(11):1131-1141 (2014); doi: 10.1021/cn5000524.
ICE Epilepsy Alliance, the Dravet Syndrome Spectrum, Nov. 2, 2008, 2 pages.
IUPHAR/BPS Guide to Pharmacology [online], "Entry for Δ 9-tetrahydrocannabidiol," available on or before Mar. 29, 2016, retrieved on Jun. 20, 2018, URL <http://www.guidetopharmacology.org/GRAC/LigandDisplayForward?tab=biology&ligandID=242>, 2 pages.
Iuvone et al., "Neuroprotective effect of cannabidiol, a non-psychoactive component from Cannabis sativa, on beta-amyloid-induced toxicity in PC12 cells," J Neurochem., 89(1):134-141 (2004).
Izzo et al., "Non-psychotropic plant cannabinoids: new therapeutic opportunities from an ancient herb," Trends in Pharmacological Sciences, 30(10):515-527 (2009).
Jacobson, "Survey of Current Cannabidiol Use in Pediatric Treatment-Resistant Epilepsy," Poster, Apr. 22, 2013, 1 page.
Jaeger, W. et al., "Inhibition of cyclosporine and tetrahydrocannabinol metabolism by cannabidiol in mouse and human microsomes," Xenobiotica, 26(3):275-284 (1996).
Jeavons et al., "Sodium valproate in treatment of epilepsy," Br Med J., 15; 2(5919):584-586 (1974).
Jones et al. [online], Info & Metrics / Article Information," Cannabidiol Displays Antiepileptiform and Antiseizure Properties in Vitro and in Vivo," J Pharmacol Exp Ther., Feb. 2010, 332(2): 569-577, retrieved on Jun. 25, 2018, URL: http://jpet.aspetjournals.org/content/332/2/569/tab-article-info, 9 pages.
Joy, et al. "Marijuana and Medicine. Assessing the Science Base." National Academy Press. Washington D.C. 1999. 170 pages.
Kahan et al., "Risk of selection bias in randomized trials," Trials, 16:405 (2015); doi: 10.1186/s13063-015-0920-x.
Kaplan, "F.D.A. Panel Recommends Approval of Cannabis-Based Drug for Epilepsy," NY Times, Apr. 19, 2018, retrieved on Jun. 20, 2018, URL <https://www.nytimes.com/2018/04/19/health/epidiolex-fda-cannabis-marajuana.html>, 3 pages.
Karler et al., "The cannabinoids as potential antiepileptics," J Clin Pharmacol, 21(8-9 Suppl): 437S-447S (1981).
Kelley et al., "Doose syndrome (myoclonic-astatic epilepsy): 40 years of progress," Developmental Medicine & Child Neurology, 52(988)-993 (2010).
Khan et al., "Key Attributes of TKDL: Laooq-e-Quinnab/Barai Zeequn-Nafs," Khazaain-al-Advia, 1911 (with English translation), 2 pages.
Khan et al., Key Attributes of TKDL: Nushka-e-Qutoor, Muheet-e-Azam, 1887 (with English translation), 2 pages.
Khan et al., "Key Attributes of TKDL: Sufoof-e-Qinnab Barae Waja," Khazaain-al-Adiva, 1911, (with English translation), 5 pages.
Khan et al., "Key Attributes of TKDL: Usaara-e-Qinnab Barai Qoolanj," Khazaain-al-Advia, 1911 (with English translation), 6 pages.
Khan et al., "Key Attributes of TKDL: Zimad-e-Qinnab," Khazaain-al-Adiva, 1911 (with English translation), 5 pages.
Klitgaard et al., "Electrophysiological, neurochemical and regional effects of levetiracetam in the rat pilocarpine model of temporal lobe epilepsy," Seizure, 12(2):92-100 (2003).

(56) References Cited

OTHER PUBLICATIONS

Klitgaard et al., "Evidence for a unique profile of levetiracetam in rodent models of seizures and epilepsy," European journal of Pharmacology, 353(2):191-206 (1998).

Kramer et al., "Febrile infection-related epilepsy syndrome (FIRES): pathogenesis, treatment, and outcome: a multicenter study on 77 children," Epilepsia, 52(11):1956-1965 (2011); doi:10.1111/j.1528-1167.2011.03250.x. Epub Aug. 29, 2011.

Kuhn et al., "Potent activity of carfilzomib, a novel, irreversible inhibitor of the ubiquitin-proteasome pathway, against preclinical models of multiple myeloma," Blood, 110(9):3281-3290 (2007).

Kwan et al., "Definition of drug resistant epilepsy: consensus proposal by the ad hoc Task Force of the ILAE Commission on Therapeutic Strategies," Epilepsia, 51(6):1069-1077 (2010); doi: 10.1111/j.1528-1167.2009.02397.x.

LeafScience.com [online], "What are the Highest CBD Strains?" Oct. 15, 2014, retrieved on Feb. 16, 2017, URL www.leafscience.com/2014/10/15/highest-cbd-strains/, 2 pages.

Leino, A. et al., "Evidence of a clinically significant drug-drug interaction between cannabidiol and tacrolimus: A case report," American Journal of Transplantation, 18 (Suppl. 4): 744-745 (2018).

Leo et al., "Cannabidiol and epilepsy: Rationale and therapeutic potential," Pharmacological Research, 107:85-92 (2016).

Lewis, "Mystery Mechanisms," The Scientist.com, Jul. 29, 2016, retrieved on Nov. 8, 2017, URL <https://www.the-scientist.com/?articles.view/articleNo/46688/title/Mystery-Mechanisms/>, 2 pages.

Lieu et al., "Assessment of self-selection bias in a pediatric unilateral hearing loss study," Otolarynzol Head Neck Surz., 142(3):427-433 (2010).

Lindamood and Colasanti, "Effects of delta 9-tetrahydrocannabinol and cannabidiol on sodium-dependent high affinity choline uptake in the rat hippocampus," J Pharmacology Experimental Therapeutics, 213(2):216-221 (1980).

Long et al., "The pharmacological actions of cannabidiol," Drugs of the Future, 30(7):747-53 (2005).

Loscher and Schmidt, "Modern antiepileptic drug development has failed to deliver: ways out of the current dilemma," Epilepsia, 52(4):657-678 (2011); doi: 10.1111/j.1528-1167.2011.03024.x.

Lowenstein, "Chapter 363: Seizures and Epilepsy," Diseases of the Central Nervous System, 2498-2512 (2008).

Lutz, "On-demand activation of the endocannabinoid system in the control of neuronal excitability and epileptiform seizures," Biochem Pharmacol, 68(9):1691-1698 (2004).

Luttjohann et al., "A revised Racine's scale for PTZ-induced seizures in rats," Physiol Behav., 98(5):579-586 (2009); doi: 10.1016/j.physbeh.2009.09.005.

Maa et al., "The case for medical marijuana in epilepsy," Epilepsia, 55(6):783-786 (2014); doi: 10.1111/epi.12610.

Mackie, "Cannabinoid receptors as therapeutic targets," Annu Rev Pharmacol Toxicol., 46:101-22 (2006).

Majoosi et al., "Key Attributes of TKDL: Saoot Baraae Sara," Kaamil-al-Sena'ah, Central Council for Research in Unani Medicine, 2005 (with English translation), 2 pages.

Malfait et al., "The nonpsychoactive cannabis constituent cannabidiol is an oral anti-arthritic therapeutic in murine collagen-induced arthritis," PNAS, 97(17):9561-9566 (2000).

Manni et al., "Obstructive Sleep Apnea in a Clinical Series of Adult Epilepsy Patients: Frequency and Features of the Comorbidity," Epilepsia, 44(6):836-840 (2003).

Manno, "Status Epilepticus: Current Treatment Strategies," The Neurohospitalist, 1(1):23-31 (2011).

Mattson et al., "Comparison of carbamazepine, phenobarbital, phenytoin, and primidone in partial and secondarily generalized tonic-clonic seizures," N. Engl. J. Med, 313(3): 145-151, Jul. 18, 1985.

Mattson et al., "Prognosis for total control of complex partial and secondary generalized tonic clonic seizures," Neurology, 47:68-76 (1996).

Mares et al., "Electrical Stimulation-Induced Models of Seizures in Model of Seizures," Chapter 12, In: Models of Seizures and Epilepsy, Philip A. Schwartzkroin & Solomon L. Moshe (eds.) 2006, 7 pages.

Marinol® Label, Unimed Pharmaceuticals, Inc., Jul. 2006, <https://www.accessdata.fda.gov/dmgsatfda docs/label/2006/018651s025s026lbl.pdf>, 11 pages.

Martin et al., "Structure-Anticonvulsant Activity Relationships of Cannabidiol Analogs," National Institute on Drug Abuse, Research Monograph Series, 79:48-58 (1987).

McCormick et al., "On the cellular and network bases of epileptic seizures," Annu Rev Physiol, 63:815-846 (2001).

McNamara, "Chapter 19: Pharmacotherapy of the Epilepsies," Goodman & Gilman's The Pharmacological Basis of Therapeutics, 11th ed., McGraw-Hill Companies, 2006, pp. 501-525.

Mechoulam et al., "Toward drugs derived from cannabis," Naturwissenschaften, 65(4):174-179 (1978).

Medicos [online]. "Convulsive Disorders and their Interference with Driving," Medicos, 2014, retrieved Feb. 10, 2017, URL <https://www.medicosporlaseguridadvial.com/en/clinical-subjects/neurologic-diseases/convulsive-disorders-and-their-interference-with-driving>, 3 pages.

Merlis, "Proposal for an International Classification of the Epilepsies," Epilepsia, 11:114-119 (1970).

Miller et al., "Mapping genetic modifiers of survival in a mouse model of Dravet syndrome," Genes, Brain and Behavior, 13:163-172 (2014).

Moral et al., "Pipeline on the Move," Drugs of the Future, Jan. 2014, 39(1): 49-56.

Morard et al., "Conversion to Sirolimus-Based Immunosuppression in Maintenance Liver Transplantation Patients," Liver Transplantation, 13:658-664 (2007).

Morelli et al., "The effects of cannabidiol and its synergism with bortezomib in multiple myeloma cell lines. A role for transient receptor potential Vanilloid type-2," Int J Cancer, 134(11):2534-2546 (2014).

MyVirtualMedicalCentre [online], "Aicardi syndrome," mvmc.com, Feb. 2004, retrieved on Jan. 25, 2019, https://www.myvmc.com/diseases/aicardi-syndrome/, 6 pages.

Nabissi et al., "Cannabinoids synergize with cafilzomib, reducing multiple myeloma cells viability and migration," Oncotarget, 7:77553 (2016).

Neto et al., "The role of polar phytocomplexes on anticonvulsant effects of leaf extracts of Lippia Alba (Mill.) N.E. Brown chemotypes," J. Pharm Pharmacol., 61(7):933-9 (2009).

Ng et al., "Illicit drug use and the risk of new-onset seizures," Am J Epidemiol., 132(1):47-57 (1990).

Oakley et al., "Dravet Syndrome Insights into pathophysiology and therapy from a mouse model of Dravet syndrome," Epilepsia, 52(Suppl. 2):59-61 (2011).

Obay et al., "Antiepileptic effects of ghrelin on pentylenetetrazole-induced seizures in rats," Peptides, 28(6):1214-1219. Epub Apr. 19, 2007.

Olyaei, A. J. et al., "Interaction Between Tacrolimus and Nefazodone in a Stable Renal Transplant Recipient," Pharmacotherapy, 18(6):1356-1359 (1998).

Pelliccia et al., [Online], "Treatment with CBD in oily solution of drug-resistant pediatric epilepsies," 2005 Congress on Cannabis and the Cannabinoids, Leiden, The Netherlands: International Association for Cannabis as Medicine, 2005, 14, retrieved on Jun. 30, 2015, URL <http//www.cannabis-med.org/studies/ww_en_db_study_show.php?s_id=173&&search_pattern=EPILEPSY>, 2 pages, Abstract only.

Pereira et al., "Study pharmacologic of the GABAergic and glutamatergic drugs on seizures and status epilepticus induced by pilocarpine in adult Wistar rats," Neurosci Lett.., 419(3):253-257 (2007). Epub Apr. 13, 2007.

Pertwee, "Cannabinoid receptor ligands: clinical and neuropharmacological considerations, relevant to future drug discovery and development," Expert Opin Investig Drugs, 9(7):1553-1571 (2000).

(56) References Cited

OTHER PUBLICATIONS

Pertwee, "The diverse CB1 and CB2 receptors pharmacology of three plant cannabinoids: Alpha9 Tetrahydrocannabinol, cannabidiol and alpha9-tetrahydrocannabivarin," BR. J. Pharmacol., 153(2): 199-215 (2008).
Pertwee, "Chapter 3: The Pharmacology and Therapeutic Potential of Cannabidiol," Cannabinoids, Ed Vincenzo Di Marzo ed., 2004, pp. 32-83.
Petrocellis et al., "Effects of cannabinoids and cannabinoid-enriched Cannabis extracts on TRP channels and endocannabinoid metabolic enzymes," British Journal of Pharmacology, 163:1479-1494 (2011).
Pohl et al., "Effects of flunarizine on Metrazol-induced seizures in developing rats," Epilepsy, 1(5):302-305 (1987).
Porter et al., "Report of a parent survey of cannabidiol-enriched cannabis use in pediatric treatment-resistant epilepsy," Epilepsy Behav., 29(3):574-577 (2013).
Porter et al., "Randomized, multicenter, dose-ranging trial of retigabine for partial-onset seizures," Neurology, 68(15):1197-1204 (2007).
Poortman-Van Der Meer, "A contribution to the improvement of accuracy in the quantitation of THC," Forensic Science International, 101(1):1-8 (1999).
Potter, "Cannabis Horticulture," Chapter 4, Handbook of Cannabis, Roger G. Pertwee (ed.), pp. 65-88 (2014).
Pouton, "Lipid formulations for oral administration of drugs: non-emulsifying, self-emulsifying and 'self-microemulsifying' drug delivery systems," Eur. J. Pharm Sci, 11(Supp. 2):S93-S98 (2000).
Press et al., "Parenteral reporting of response to oral cannabis extracts for treatment of refractory epilepsy," Epilepsy Behav, 45:49-52 (2015).
Pruitt et al., "Ethanol in Liquid Preparations Intended for Children," Pediatrics, 73(3):405-407 (1984).
Raab et al., "Multiple myeloma," Lancet, 374(9686):314-339 (2009).
Rabinski [online], "CBD-A: Cannabidiol Acid Cannabinoid Profile," MassRoots, Jul. 2, 2015, retrieved on Jan. 31, 2018, URL <https://www.massroots.com/learn/can-the-cbd-a-cannabinoid-help-you/>, 4 pages.
Ramantani et al., "Epilepsy in Aicardi—Goutières Syndrome," Official J Eur Paediatric Neurology Society, 18:30-37 (2014).
Rauca et al., "The role of superoxide dismutase and alpha-tocopherol in the development of seizures and kindling induced by pentylenetetrazol—influence of the radical scavenger alpha-phenyl-N-tert-butyl nitrone," Brain Research, 1009(1-2):203-212 (2004).
Resstel et al. "5-HT1A receptors are involved in the cannabidiol-induced attenuation of behavioural and cardiovascular responses to acute restraint stress in rats," Br J Pharmacol., 156(1):181-188 (2009).
Rosenberg et al., "Cannabinoids and Epilepsy," Neurotherapeutics, 12(4):747-768 (2015).
Rosenkrantz et al., "Oral and Parenteral Formulations of Marijuana Constituents," J Pharm Sci, 61(7):1106-1112 (1972).
Rubio et al., "In vivo Experimental Models of Epilepsy," Central Nervous System Agents in Medicinal Chemistry, 10:298-309 (2010).
Russo, "Taming THC: potential cannabis synergy and phytocannabinoid-termoid entourage effects," British J. of Pharm., 163:1333-1364 (2011).
Sadanandasarma et al., "Key Attributes of TKDL: Suddha Bhanga Visista Gunah Aur Matra," Rasatarangini 11th Ed., 720-723 (with English translation), 8 pages.
Sander, "The epidemiology of epilepsy revisited," Curr Opin Neural, 16(2):165-170 (2003).
Sastri et al., "Key Attributes of TKDL: Vijaya Kalpah (Apasmaranasaka)," Anandakandam 1st ed., 1952:241 (with English translation), 5 pages.
Scuderi et al., "Cannabidiol in medicine: a review of its therapeutic potential in CNS disorders," Phytother Res., 23(5):597-602 (2009).
Silva et al., "Clobazam as Add-on Therapy in Children with Epileptic Encephalopathy," Can. J. Neurol. Sci., 33:209-213 (2006).
Shukla [online], "New Automated Purification Strategies for Scale-Up," PCISyntesis.com, posted Dec. 25, 2017, https://www.pcisynthesis.com/new-automated-purification-strategies-for-scale-up/, 5 pages.

Sperling et al., "Carisbamate as adjunctive treatment of partial onset seizures in adults in two randomized, placebo-controlled trials," Epilepsia, 51(3):333-343 (2010).
Stafstrom et al., "Models of Pediatric Epilepsies: Strategies and Opportunities," Epilepsia, 47(8): 1407-1414 (2006).
Stephenson, "In Memoriam: Professor Jean Aicardi (1926-2015)," Pediatric Neurology, 54:3-4 (2016).
Stott et al., "Cannabinoids for the pharmaceutical industry," Euphytica, 140:83-93 (2004).
Strickley, "Solubilizing Excipients in Oral and Injectable Formulations," Table VIII, Pharmaceutical Research, 21(2):201-230 (2004).
Swann et al., "The effects of seizures on the connectivity and circuitry of the developing brain," Ment Retard Dev Disabil Res Rev., 10(2):96-100 (2004).
Thomas et al., "Evidence that the plant cannabinoid Delta9-tetrahydrocannabivarin is a cannabinoid CBI and CB2 receptor antagonist," Br J Pharmacol., 146(7):917-926 (2005).
Thumma et al., "Influence of plasticizers on the stability and release of a prodrug of ./19-tetrahydrocannabinol incorporated in poly (ethylene oxide) matrices," Eur J Pharmaceutics and Biopharmaceutics, 70(2):605-614 (2008).
Thurman et al., "Standards for epidemiologic studies and surveillance of epilepsy," Epilepsia, 52 (Suppl 7):2-26 (2011).
Thurston, "Avoid Charlotte's Web for Epilepsy," Jun. 26, 2014, URL <http://drthurstone.com/charlotted-web-not-safest-option-epilepsy-treatment/>, 4 pages.
Trembly & Sherman, "Double-blind clinical study of cannabidiol as a secondary anticonvulsant," Marijuana '90 Int. Conf. on Cannabis and Cannabinoids, Kolympari (Crete), Jul. 8-11, 1990, 1 page, Abstract only.
Turkanis et al., "An Electrophysiological Analysis of the Anticonvulsant Action of Cannabidiol on Limbic Seizures in Conscious Rats," Epilepsia, 20:351-363 (1979).
U.S. Department of Health and Human Services, Food and Drug Administration Center for Drug Evaluation and Research (CDER), "Guidance for Industry Estimating the Maximum Safe Starting Dose in Initial Clinical Trials for Therapeutics in Adult Healthy Volunteers," Jul. 2005, 30 pages.
Usami et al., "Synthesis and pharmacological evaluation in mice of halogenated cannabidiol derivatives," Chem Pharm Bull (Tokyo), 47(11):1641-1645 (1999).
Utah.gov [online], "2nd Agenda Controlled Substances Advisory Committee Meeting," Nov. 12, 2013, URL <https://www.utah.gov/pmn/files/81459.pdf>, 63 pages.
Van Rijckevorsel, "Treatment of Lennox-Gastaut Syndrome: overview and recent findings," Neuropsychiatr Dis Treat, 4(6):1001-1019 (2008).
Velasco et al., "Anticancer mechanisms of cannabinoids," Curr Oncol, 23(2):S23-S32 (2016).
Velisek, "Chapter 11: Models of Chemically-Induced Acute Seizures," Models of Seizures and Epilepsy, pp. 127-152 (2006).
Veliskova, "Chapter 48: Behavioral Characterization of Seizures in Rats," Models of Seizures and Epilepsy, pp. 601-611 (2006).
Vollner et al., "Haschisch XX+[Haschisc XX+]: Cannabidivarin, a new hashish substance," Tetrahedron Letters, 10(3):145-147 (1969).
Wahle et al., "Development of Tolerance to the Anticonvulsant Effect of Valproate but not to Ethosuximide in a Rat Model of Absence Epilepsy," Eur J Pharma, 181(1-2):1-8 (1990).
Wallace et al., "Pharmacotherapy for Dravet Syndrome," Pediatr. Drugs, 18:197-208 (2016).
Wallace et al., "Assessment of the role of CB 1 receptors in cannabinoid anticonvulsant effects," Eur J Pharmacol., 428(1):51-57 (2001).
Weimer-Kruel, A. et al., "Cannabidiol Interacts Significantly with Everolimus—Report of a Patient with Tuberous Sclerosis Complex," Neuropediatrics, 50(6), 2019, 4 pages; doi:https://doi.org/10.1055/s-0039-1695786.
Weston et al., "Tetrahydrocannabivarin exhibits anticonvulsant effects in a piriform cortical brain slice model of epileptiform activity," Proceedings of the British Pharm Society, Dec. 2006, retrieved on Mar. 1, 2017, URL <http://www.pA2online.org/abstrat/abstract.jsp?abid=28533>, 1 page, Abstract only.

(56) References Cited

OTHER PUBLICATIONS

Wingerchuk, "Cannabis for medical purposes: cultivating science, weeding out the fiction," Lancet, 364:315-316 (2004).
Yamaori, S. et al., "Potent inhibition of human cytochrome P450 3A isoforms by cannabidiol: Role of phenolic hydroxyl groups in the resorcinol moiety," Life Sciences, 88:730-736 (2011).
Yu et al., "Reduced sodium current in GABAergic interneurons in a mouse model of severe myoclonic epilepsy in infancy," Nature Neuroscience, 9(9):1142-1149 (2006).
Yuriev, "Endogenic cannabinoid system is a new perspective object of pharmacotherapeutic effect to disease of nervous system," Ukrainsky Mnemotechny Chasopis, 6(50):21-29 (2005) (with English Abstract).
Zhao et al., "Chapter 27: Repetitive Seizures in the Immature Brain," Models of Seizures and E[epilepsy, 341-350 (2006).
Zhornitsky & Potvin, "Cannabidiol in Humans—The Quest for Therapeutic Targets," Pharmaceuticals, 5:529-552 (2012).
Zuardi et al., "Cannabidiol, a Cannabis sativa constituent, as an antipsychotic drug," Braz J Med Biol Res., 39(4):421-429 (2006).
Zuardi et al., "Cannabidiol: from an inactive cannabinoid to a drug with wide spectrum of action," Rev Bras Psiquiatr, 30(3):271-280 (2008).
U.S. Appl. No. 15/640,033, filed Jun. 30, 2017; Inventor(s): Jitinder Wilkhu et al.
U.S. Appl. No. 16/959,354, filed Jun. 30, 2020; Inventor(s): Jitinder Wilkhu et al.
U.S. Appl. No. 16/935,005, filed Jul. 21, 2020; Inventor(s): Geoffrey Guy et al.
U.S. Appl. No. 17/012,448, filed Sep. 4, 2020; Inventor(s): Benjamin Whalley et al.
U.S. Appl. No. 17/050,956, filed Oct. 27, 2020; Inventor(s): Geoffrey Guy et al.
U.S. Appl. No. 17/102,109, filed Nov. 23, 2020; Inventor(s): Guillermo Velasco Diez et al.
U.S. Appl. No. 17/231,625, filed Apr. 15, 2021; Inventor(s): Stephen Wright et al.
U.S. Appl. No. 17/296,066, filed May 21, 2021; Inventor(s): Geoffrey Guy et al.
U.S. Appl. No. 17/296,076, filed May 21, 2021; Inventor(s): Geoffrey Guy et al.
U.S. Appl. No. 17/424,682, filed Jul. 21, 2021; Inventor(s): Geoffrey Guy et al.
U.S. Appl. No. 17/426,442, filed Jul. 28, 2021; Inventor(s): Geoffrey Guy et al.
U.S. Appl. No. 17/406,401, filed Aug. 19, 2021; Inventor(s): Jitinder Wilkhu et al.
U.S. Appl. No. 17/435,892, filed Sep. 2, 2021; Inventor(s): Geoffrey Guy et al.
U.S. Appl. No. 17/606,370, filed Oct. 25, 2021; Inventor(s): Geoffrey Guy et al.
U.S. Appl. No. 17/611,824, filed Nov. 16, 2021; Inventor(s): Geoffrey Guy et al.
U.S. Appl. No. 17/548,232, filed Dec. 10, 2021; Inventor(s): Stephen Wright et al.
U.S. Appl. No. 17/576,868, filed Jan. 14, 2022; Inventor(s): Benjamin Whalley et al.
U.S. Appl. No. 17/627,946, filed Jan. 18, 2022; Inventor(s): Alan James Silcock et al.
U.S. Appl. No. 17/585,415, filed Jan. 26, 2022; Inventor(s): Benjamin Whalley et al.
U.S. Appl. No. 17/631,069, filed Jan. 28, 2022; Inventor(s): Geoffrey Guy et al.
U.S. Appl. No. 17/638,629, filed Feb. 25, 2022; Inventor(s): Benjamin Whalley et al.
U.S. Appl. No. 17/689,607, filed Mar. 8, 2022; Inventor(s): Geoffrey Guy et al.
U.S. Appl. No. 17/689,245, filed Mar. 8, 2022; Inventor(s): Harshit Shah et al.
U.S. Appl. No. 17/768,048, filed Apr. 11, 2022; Inventor(s): Geoffrey Guy et al.
U.S. Appl. No. 17/770,435, filed Apr. 20, 2022; Inventor(s): Geoffrey Guy et al.
U.S. Appl. No. 17/770,436, filed Apr. 20, 2022; Inventor(s): Geoffrey Guy et al.
U.S. Appl. No. 17/771,184, filed Apr. 22, 2022; Inventor(s): Geoffrey Guy et al.
U.S. Appl. No. 17/771,190, filed Apr. 22, 2022; Inventor(s): Geoffrey Guy et al.
U.S. Appl. No. 17/771,195, filed Apr. 22, 202; Inventor(s): Geoffrey Guy et al.
U.S. Appl. No. 17/771,183, filed Apr. 22, 2022; Inventor(s): Geoffrey Guy et al.
U.S. Appl. No. 17/744,224, filed May 13, 2022; Inventor(s): Geoffrey Guy et al.
U.S. Appl. No. 17/777,734, filed May 18, 2022; Inventor(s): Geoffrey Guy et al.
U.S. Appl. No. 17/777,677, filed May 18, 2022; Inventor(s): Geoffrey Guy et al.
U.S. Appl. No. 17/777,681, filed May 18, 2022; Inventor(s): Geoffrey Guy et al.
U.S. Appl. No. 17/841,167, filed Jun. 15, 2022; Inventor(s): Geoffrey Guy et al.
U.S. Appl. No. 17/786,949, filed Jun. 17, 2022; Inventor(s): Alan James Silcock et al.
U.S. Appl. No. 17/853,367, filed Jun. 29, 2022; Inventor(s): Geoffrey Guy et al.
U.S. Appl. No. 17/817,753, filed Aug. 5, 2022; Inventor(s): Volker Knappertz et al.
U.S. Appl. No. 18/002,437, filed Dec. 19, 2022; Inventor(s): Jie Li et al.
U.S. Appl. No. 18/005,838, filed Jan. 17, 2023; Inventor(s): Daniel Adam Checketts et al.
U.S. Appl. No. 18/005,841, filed Jan. 17, 2023; Inventor(s): Daniel Adam Checketts et al.
U.S. Appl. No. 18/005,843, filed Jan. 17, 2023; Inventor(s): Daniel Adam Checketts et al.
U.S. Appl. No. 18/005,845, filed Jan. 17, 2023; Inventor(s): Daniel Adam Checketts et al.
U.S. Appl. No. 18/005,847, filed Jan. 17, 2023; Inventor(s): Daniel Adam Checketts et al.
U.S. Appl. No. 18/005,848, filed Jan. 17, 2023; Inventor(s): Daniel Adam Checketts et al.
U.S. Appl. No. 18/005,851, filed Jan. 18, 2023; Inventor(s): Daniel Adam Checketts et al.
U.S. Appl. No. 18/005,852, filed Jan. 18, 2023; Inventor(s): Daniel Adam Checketts et al.
U.S. Appl. No. 18/005,853, filed Jan. 18, 2023; Inventor(s): Daniel Adam Checketts et al.
U.S. Appl. No. 18/005,868, filed Jan. 18, 2023; Inventor(s): Daniel Adam Checketts et al.
U.S. Appl. No. 18/005,959, filed Jan. 18, 2023; Inventor(s): Daniel Adam Checketts et al.
U.S. Appl. No. 18/005,960, filed Jan. 18, 2023; Inventor(s): Daniel Adam Checketts et al.
U.S. Appl. No. 18/005,961, filed Jan. 18, 2023; Inventor(s): Daniel Adam Checketts et al.
U.S. Appl. No. 18/006,121, filed Jan. 19, 2023; Inventor(s): Daniel Adam Checketts et al.
U.S. Appl. No. 18/006,125, filed Jan. 19, 2023; Inventor(s): Daniel Adam Checketts et al.
U.S. Appl. No. 18/006,127, filed Jan. 19, 2023; Inventor(s): Daniel Adam Checketts et al.
U.S. Appl. No. 18/006,129, filed Jan. 19, 2023; Inventor(s): Daniel Adam Checketts et al.
U.S. Application No. 18,006,131, filed Jan. 19, 2023; Inventor(s): Daniel Adam Checketts et al.
U.S. Application No. 18,006,133, filed Jan. 19, 2023; Inventor(s): Daniel Adam Checketts et al.
U.S. Appl. No. 18/161,603 filed Jan. 30, 2023; Inventor(s): William Hind et al.
U.S. Appl. No. 18/170,235, filed Feb. 16, 2023; Inventor(s): Geoffrey Guy et al.

(56) References Cited

OTHER PUBLICATIONS

U.S. Appl. No. 18/043,810, filed Mar. 2, 2023; Inventor(s): Michael Simon Loft et al.
U.S. Appl. No. 18/044,941, filed Mar. 10, 2023; Inventor(s): Kevin James Craig et al.
U.S. Appl. No. 18/245,856, filed Mar. 17, 2023; Inventor(s): Kevin James Craig et al.
U.S. Appl. No. 18/186,792, filed Mar. 20, 2023; Inventor(s): Geoffrey Guy et al.
U.S. Appl. No. 18/311,221, filed May 2, 2023; Inventor(s): Geoffrey Guy et al.
U.S. Appl. No. 18/256,307, filed Jun. 7, 2023; Inventor(s): Daniel Adam Checketts et al.
U.S. Appl. No. 18/257,373, filed Jun. 14, 2023; Inventor(s): Alan James Silcock et al.
U.S. Appl. No. 18/257,537, filed Jun. 14, 2023; Inventor(s): Alan James Silcock et al.
U.S. Appl. No. 18/257,479, filed Jun. 14, 2023; Inventor(s): Karen Ka-Yen Tse et al.
U.S. Appl. No. 18/258,485, filed Jun. 20, 2023; Inventor(s): Kevin James Craig et al.
U.S. Appl. No. 18/446,405, filed Aug. 8, 2023; Inventor(s): Geoffrey Guy et al.
U.S. Appl. No. 18/546,254, filed Aug. 11, 2023; Inventor(s): Karen Ka-Yen Tse et al.
U.S. Appl. No. 18/548,003, filed Aug. 25, 2023; Inventor(s): Volker Knappertz et al.
U.S. Appl. No. 18/477,467, filed Sep. 28, 2023; Inventor(s): Jitinder Wilkhu et al.
U.S. Appl. No. 18/479,671, filed Oct. 2, 2023; Inventor(s): Alan James Silcock et al.
U.S. Appl. No. 18/560,316, filed Nov. 10, 2023; Inventor(s): Alan James Silcock et al.
U.S. Appl. No. 18/560,337, filed Nov. 10, 2023; Inventor(s): Alan James Silcock et al.
U.S. Appl. No. 18/560,341, filed Nov. 10, 2023; Inventor(s): Alan James Silcock et al.
U.S. Appl. No. 18/560,346, filed Nov. 10, 2023; Inventor(s): Alan James Silcock et al.
U.S. Appl. No. 18/526,795, filed Dec. 1, 2023; Inventor(s): Geoffrey Guy et al.
U.S. Appl. No. 18/545,754, filed Dec. 19, 2023; Inventor(s): Geoffrey Guy et al.
U.S. Appl. No. 18/292,844, filed Jan. 26, 2024; Inventor(s): Volker Knappertz et al.
U.S. Appl. No. 18/597,717, filed Mar. 6, 2024; Inventor(s): Jonathan Oliver Whitehouse et al.
U.S. Appl. No. 61/969,070, filed Mar. 21, 2014, Kane et al.
U.S. Appl. No. 62/004,495, filed May 29, 2014, Vangara et al.
U.S. Appl. No. 62/154,660, filed Apr. 29, 2015, Vangara et al.
U.S. Appl. No. 14/724,351, filed May 28, 2015, Vangara et al.
Abati, E. et al., "Cannabidiol treatment of refractory epileptic spasms: an open label study," American Epilepsy Society, Annual Meeting, Abstract 3.404, 2015, 2 pages; https://aesnet.org/abstractslisting/cannabidiol-treatment-of-refractory-epileptic-spasms--an-open-label-study.
Aagaard, L. et al., "Adverse Drug Reactions in the Paediatric Population in Denmark: A Retrospective Analysis of Reports Made to the Danish Medicines Agency from 1998 to 2007," Drug Saf, 33(4):327-339 (2010).
Adams, R. et al., "Isolation of Cannabinol, Cannabidiol and Quebrachitol from Red Oil of Minnesota Wild Hemp," J. Am. Chem. Soc. 1940, 62, 8, 2194-2196.
|Aker, R. G. et al., "Chemically Induced Experimental Models of Absence Epilepsy," Chemical-Induced Seizures: Mechanisms, Consequences and Treatment, Chapter 6, 2011, pp. 67-79.
Akiyama, M. et al., "Dravet Syndrome: A Genetic Epileptic Disorder," Acta. Med. Okayama, 66(5):369-376 (2012).
Allen, J. W., "Clobazam as an adjunctive treatment in refractory epilepsy," British Medical Journal, 286:1246-1247 (1983).

Anderson, C. L., "An Evaluation of Effectivness of Cannabidiol as an Antiepileptic Drug for Children with Intractable Generalized Epilepsy," Dissertation, University of Florida, 2017, 130 pages; https://ufdc.ufl.edu/UFE0050852/00001/pdf.
Arik, A. E. et al., "Effect of levetiracetam on penicillin induced epileptic activity in rats," Acta Neurobiol Exp, 74:266-275 (2014).
|Allen G., "Florida Bill Would Allow Medical Marijuana For Child Seizures," Jan. 16, 2014, retrieved from https://www.npr.org/sections/health-shots/2014/01/16/262481852/florida-bill-would-allow-marijuana-extract-for-child-seizures, 16 pages.
[Anonymous], "GW Pharma—GW Pharmaceuticals Announces New Physician Reports of Epidiolex® Treatment Effect in Children and Young Adults With Treatment-Resistant Epilepsy," Oct. 14, 2014; https://ir.gwpharm.com/news-releases/news-release-details/gw-pharmaceuticals-announces-new-physician-reports-epidiolexr-0, 4 pages.
[Anonymous], "Gw Pharmaceuticals Announces Epidiolex Receives Fast Track Designation from FDA for the Treatment of Dravet Syndrome," GW Pharmaceuticals Press Release dated Jun. 6, 2014; http://www.gwpharm.com/GW%20Pharmaceuticals%20Announces%20Epidiolex%20Receives%20Fast%20Track%20Designation%20from%20FDA%20for%20the%20Treatment%20of%20Dravet%20Syndrome.aspx, 5 pages.
[Anonymous], "Salutaris Drops Buy Salutaris Drops—Salutaris Drops," Oct. 12, 2014; http://web.archive.org/web/20141012130255/http://salutarisdrops.com/buy-salutaris-drops/, 2 pages.
[Anonymous], "Salutaris Drops Cannabidiol for Aicardi Syndrome—Salutaris Drops," Oct. 12, 2014; http:/web.archive.org/web/20141012220050/http://salutarisdrops.com/cannabidiol-aicardi-syndrome/, 3 pages.
[Anonymous], "GW Pharma Initiates Second Phase 3 Pivotal Study of Epidiolex® (CBD) in Lennox-Gastaut Syndrome," Jun. 11, 2015; https://www.benzinga.com/pressreleases/18/11/g12748407/gw-pharmaceuticals-announces-second-positive-phase-3-pivotal-trial-for, 5 pages.
Approval Letter for NDA 210365 Epidiolex, Jun. 25, 2018, 12 pages.
Arzimanoglou et al., "All children who experience epileptic falls do not necessarily have Lennox-Gastaut syndrome . . . but many do," Epileptic Disord. 2011, 13: S3-S13 (2011).
[No Author Listed], "ILAE Proposal for Revised Terminology for Organization of Seizures and Epilepsies," 2010, 2 pages.
[No Author Listed] "Orphan Drug Designation Granted for Epidiolex in Dravet syndrome by the FDA-Seven Expanded Access INDs granted by FDA to US physicians to treat with Epidiolex 125 children suffering from intractable epilepsy syndromes," GW Pharmaceuticals Press Release dated Nov. 14, 2013, 3 pages.
[No Author Listed] GW Pharmaceuticals Provides Update on Orphan Program in Childhood Epilepsy for Epidiolex, GW. Pharm. Available online Nov. 14, 2013, Retrieved Feb. 10, 2017, 5 pages.
[No Author Listed] "What are the Highest CBD Strains?" accessed Feb. 16, 2017, published Oct. 15, 2014, 2 pages.
[No Author Listed] "Convulsive Disorders and Their Interference with Driving," Medicos., Retrieved Feb. 10, 2017, Retrieved from internet: URL https://www.medicosporlaseguridadvial.com/en/clinical-subjects/neurologic-diseases/convulsive- disorders-and-their-interference-with-driving/, 2014, 3 pages.
[No Author Listed] "Estimating the Maximum Safe Starting Dose in Initial Clinical Trials for Therapeutics in Adult Healthy Volunteers," FDA Guidance for Industry, Jul. 2005, 30 pages.
[No Author Listed] "Gw Pharmaceuticals Announces Physician Reports of Epidiolex Treatment Effect in Children and Young Adults with Treatment-resistant epilepsy from Physician-Led Expanded Access Treatment Program," GW Pharmaceuticals Press Release dated Jun. 17, 2014, 2 pages.
[No Author Listed], "High Rollers Bet On Cannabidiol (CBD)—Medical Marijuana Patients Come Up Short," Mar. 3, 2013, 9 pages; https://www.420magazine.com/community/threads/high-rollers-bet-on-cannabidiol-cbd-%E2%80%94-medical-marijuana-patients-come-up-short.185325/.
[No Author Listed], "Selected Media Examples Of Pediatric Applications OfCannabidiol (CBD)," Jun. 30, 2013, 4 pages; https://www.420magazine.com/community/threads/selected-media-examples-of-pediatric-applications-of-cannabidiol-cbd.192155/.

(56) References Cited

OTHER PUBLICATIONS

[No Author Listed], "Medical Marijuana For N.J. Children? It's All In Gov. Christie's Hands," CBS News New York, Jun. 27, 2013, 3 pages; https://www.cbsnews.com/newyork/news/medical-marijuana-for-n-j-children-its-all-in-gov-christies-hands/.

[No Author Listed], "Photo Release—Kannaway Back office Goes Live CBD-Rich Hemp Oil Products Offered for Sale," May 7, 2014, Globe Newswire, https://www.globenewswire.com/en/news-release/2014/05/07/634020/30927/en/Photo-Release-Kannaway-Back-Office-Goes-Live-CBD-Rich-Hemp-Oil-Products-Offered-for-Sale.html, 6 pages.

[No Author Listed], GW and Otsuka Enter into Gobal Cannabinoid Research Collaboration, News Release, Jul. 9, 2007; https://www.otsuka.co.jp/en/company/newsreleases/2007/20070709_1.html, 4 pages.

[No Author Listed], License Agreement between GW Pharma and GW Pharmaceuticals, PLC and Otsuka, Feb. 2007; https://www.sec.gov/Archives/edgar/data/1351288/000104746913003351/a2213875zex-10_16.htm, 63 pages.

Amada, N. et al., "Cannabidivarin (CBDV) suppresses pentylenetetrazole (PTZ)-induced increases in epilepsy-related gene expression," 2013, PeerJ, 1: e214; 18 pages; http://dx.doi.org/10.7717/peerj.214.

AAN 67th Annual Meeting Abstract, Apr. 2015; https://www.aan.com/PressRoom/Home/GetDigitalAsset/11570, 1 page.

Andre, E. S. et al., "Spontaneous absence-like activity in Wistar rats: Behavioral and electrographic characteristics and the effects of antiepileptic drugs," Acta Scientiarum. Biological Sciences, 36(2):231-239 (2014).

Astruc-Diaz, F., "Cannabinoids delivery systems based on supramolecular inclusion complexes and polymeric nanocapsules for treatment of neuropathic pain," Université Claude Bernard—Lyon I, 2012, submitted on Jan. 23, 2014; https://tel.archives-ouvertes.fr/tel-00935588 [accessed Nov. 1, 2019], 278 pages.

Babayeva et al., "Marijuana Compounds: A Non-Conventional Therapeutic Approach to Epilepsy in Children," J. Addict. Neuropharmacol, 1:1 (2014); doi: 10.24966/AAD-7276/100002, 9 pages.

Bacca, A., "HempVap from HempMedsPX," Mar. 10, 2014; https://cannabisnow.com/hempvap-from-hempmedspx/, 3 pages.

Barton, M. E. et al., "Pharmacological characterization of the 6 Hz psychomotor seizure model of partial epilepsy," Epilepsy Research, 47:217-227 (2001).

Ben-Ari, Y., "Seizures Beget Seizures: The Quest for GABA as a Key Player," Critical Reviews in Neurobiology, 18(1-2):135-144 (2006).

Bhattacharyya, S. et al., "Opposite Effects of delta-9-Tetrahydrocannabinol and Cannabidiol on Human Brain Function and Psychopathology," Neuropsychopharmacology, 35:764-774 (2010).

Bell, J., "Treatment With CBD In Oily Solution Of Drug-Resistant Paediatric Epilepsies," Oct. 18, 2011, 3 pages; https://www.420magazine.com/community/threads/treatment-with-cbd-in-oily-solution-of-drug-resistant-paediatric-epilepsies.154896/.

Benowitz & Jones "Cardiovascular and metabolic considerations in prolonged cannabinoid administration in man," J Clin Pharm, 21:214S-223S, 1981.

Bergamaschi, M. M. et al., "Safety and Side Effects of Cannabidiol, a Cannabis sativa Constituent," Current Drug Safety, 6:237-249 (2011).

Bialer, M. & White, S., "Key factors in the discovery and development of new antiepileptic drugs," Nat Rev Drug Discov, 9(1):68-82 (2010); doi: 10.1038/nrd2997.

Bienenstock, D., "A Comprehensive History of Marijuana's Epilepsy-Treating Compound, CBD," Jun. 2014, Vice Article, retrieved from https://www.vice.com/da/article/mv53yp/desperately-seeking-cbd, 17 pages.

Bijnsdorp, I. V. et al., "Analysis of Drug Interactions," Chapter 34, Cancer Cell Culture, Methods in Molecular Biology, Second Edition, Ian A. Cree, Ed., 2011:731:421-34, 19 pages.

Bowman et al., "Epilepsy," Encyclopedia of Life Sciences, 1, 2001; www.els.net, 8 pages.

Bromfield, E. B., Cavazos, J. I., Sirven (Ed.,), An Introduction to Epilepsy [Internet], West Hartford, CT, American Epilepsy Society; 2006, PMID: 20821849, 187 pages.

Gardner, "Cannabidiols: Potential Use in Epilepsy & Other Neurological Disorders." Cannabidiol Conference at NYU School of Medicine, Oct. 2013. NYU Langone Health. Retrieved from the Internet Nov. 2019. <URL: http://faces.med.nyu.edu/research-education/cannabidiol-conference>, 4 pages.

Camfield, "Definition and natural history of Lennox-Gastaut Syndrome," Epilepsia, 52:3-9 (2011).

Campos-Castello, "Rational approach to treatment options for Lennox-Gastaut syndrome," Orphanet, Mar. 2003; https://www.orpha.net/data/patho/GB/uk-Lennox.pdf, 5 pages.

|Capal, J. K. & Franz, D. N., "Profile of everolimus in the treatment of tuberous sclerosis complex: an evidence-based review of its place in therapy," Neuropsychiatric Disease and Treatment, 12:2165-2172 (2016).

Carlini, E. A. et al., "Letter: Cannabidiol and Cannabis sativa extract protect mice and rats against convulsive agents," J Pharm Pharmacol. Aug. 1973;25(8):664-5. doi: 10.1111/j.2042-7158.1973.tb10660.x.

Carlini, E. A. et al., "Anticonvulsant Activity of Four Oxygenated Cannabidiol Derivatives," Research Communications in Chemical Pathology and Pharmacology, 12(1), Sep. 1975, 15 pages.

Carvill, G. L. et al., "GABRA1 and STXBP1: Novel generic causes of Dravet Syndrome," Neurology, 82:1245-1253 (2014).

Chesney et al., "Adverse effects of cannabidiol: a systematic review and meta-analysis of randomized clinical trials, " Neuropsychopharmacol., 45:1799-1806 (2020); https://doi.org/10.1038/s41386-020-0667-2.

Chiron, S., "Stiripentol for the treatment of Dravet syndrome," Orphan Drugs: Research and Reviews, 4:29-38 (2014).

Cholongitas et al., "Systematic review: The model for end-stage liver disease—should it replace Child-Pugh's classification for assessing prognosis in cirrhosis?" Aliment Pharmacol Ther, 22(11-12):1079-89 (2005); doi: 10.1111/j.1365-2036.2005.02691.x..

Chou, T.-C., "Drug Combination Studies and Their Synergy Quantification Using the Chou-Talalay Method," Cancer Res, 70(2):440-446 (2010).

Chu-Shore, C. J. et al., "The natural history of epilepsy in tuberous sclerosis complex," Epilepsia, 51(7):1236-1241, 2010; doi: 10.1111/j.1528-1167.2009.02474.

Ciccone, "Drop Seizure Frequency in Lennox-Gastaut Decrease With Cannabidiol," Neurology Advisor, Apr. 26, 2017; retrieved from the Internet: URL: https://neurologyadvisor.com/aan-2017-coverage/aan-2017-cannabidiol-reduces-drop-seizures-in-lennox-gasaut-syndrome/article/652931, 6 pages.

|Cilio, Maria Roberta, M.D., Ph.D. of the Pediatric Epilepsy and Clinical Neurophysiology for the University of California, San Francisco presents her talk on "CBD in Children with Treatment-Resistant Epilepsies: Planned Trials in Dravet and Lennox-Gastaut Syndromes," at NYU School of Medicine's Cannabidiol Conference (Oct. 4, 2013). Video published online. <http://faces.med.nyu.edu/research-education/cannabidiol-conference>, 44 pages.

Cilio, M. R. et al., "The case for assessing cannabidiol I epilepsy," Epilepsia, 55(6):787-790 (2014).

Citti et al., "Pharmaceutical and biomedical analysis of cannabinoids: A critical review," Journal of Biopharmaceutical and Biomedical Analysis, 147:565-579 (2018).

Clinical trials.gov [online], Identifier: NCT02224690, A Study to Investigate the Efficacy and Safety of Cannabidiol (GWP42003-P; Cbd) as Adjunctive Treatment for Seizures Associated With Lennox-Gastaut Syndrome in Children and Adults (GWPCARE4) Jazz Pharmaceuticals, U.S. National Library of Medicine, last update posted Sep. 8, 2022, 3 pages; Retrieved from https://clinicaltrials.gov/ct2/show/NCT02224690.

Clinical trials.gov [online], Identifier: NCT02091206, A Dose Ranging Pharmacokinetics and Safety Study of GWP42003-P in Children With Dravet Syndrome (GWPCARE1), Jazz Pharmaceuticals, U.S. National Library of Medicine, last update posted Sep. 28, 2022, 9 pages; Retrieved from https://clinicaltrials.gov/ct2/show/NCT02091206.

Clinical trials.gov [online], Identifier: NCT02006628, A study to compare the change in symptom severity in participants with

(56) References Cited

OTHER PUBLICATIONS schizophrenia or related psychotic disorder when treated with GWP42003 or placebo in conjunction with existing anti-psychotic therapy over a period of six weeks, Jazz Pharmaceuticals, U.S. National Library of Medicine, last update posted Sep. 28, 2022, 9 pages; Retrieved from https://clinicaltrials.gov/ct2/show/NCT02006628.
Clinical trials.gov [online], Identifier: NCT02091375, Antiepileptic Efficacy Study of GWP42003-P in Children and Young Adults With Dravet Syndrome (GWPCARE1), Jazz Pharmaceuticals, U.S. National Library of Medicine, last update posted Sep. 28, 2022, 40 pages; Retrieved from https://www.clinicaltrials.gov/ct2/show/NCT02091375.
ClinicalTrials.gov archive, History of Changes for Study: NCT02324673, National Institute of Health U.S. National Library of Medicine (Dec. 19, 2014), https://classic.clinicaltrials.gov/ct2/history/NCT02324673?V_1=View#StudyPageTop, 13 pages.
Collins, T. R., "What Neurologists are Doing About Medical Marijuana?" Neurology Today, Apr. 17, 2014, vol. 4, issue 8, 8 pages.
Consroe, et al., "Controlled clinical trial of cannabidiol in Huntington's Disease," Pharmacology Biochemistry & Behavior, 40:701-708 (1991).
Consroe et al., "Therapeutic Potential of Cannabinoids in Neurological Disorders," Cannabonioids as Therapeutic Agents, R. Mechoulam, Ed., 1986, pp. 21-49.
Consroe et al., "Open label evaluation of cannabidiol in dystonic movement disorders," International Journal of Neuroscience, 30(4):277-282 (1986); doi: 10.3109/00207458608985678.
Consroe et al., "Antiepileptic Potential of Cannabidiol Analogs," J Clin Pharmacol., 21:428S-436S (1981).
Consroe et al., "Assay of Plasma Cannabidiol by Capillary Gas Chromatography/Ion Trap Mass Spectroscopy Following High-Dose Repeated Daily Oral Administration in Humans," Pharmacology Biochemistry & Behavior, 40:517-522 (1991).
Costa, B et al., "Oral anti-inflammatory activity of cannabidiol, a non-psychoactive constituent of cannabis, in acute carrageenan-induced inflammation in the rat paw," Naunyn-Schmiedeberg's Arch Pharmacol, 369:294-299 (2004).
Cotter, B., "Medicinal marijuana stops seizures, brings hope to little girl," The Gazette, Jun. 9, 2013, 8 pages; https://gazette.com/health/medicinal-marijuana-stops-seizures-brings-hope-to-a-little-girl/article_520b074e-5c46-5d75-af95-bdd060f4a8b9.html.
Cotterell, A., "How One Young Girl Could Change Idaho's Strict Marijuana Laws," Jun. 17, 2014; https://www.knkx.org/law/2014-06-19/how-one-young-girl-could-change-idahos-strict-marijuana-laws, 8 pages.
Crowther et al., "The Medication of Cannabis," The transcript of a Witness Seminar held by the Wellcome Trust Centre for the History of Medicine at UCL, London, on Mar. 24, 2009; http://qmro.qmul.ac.uk/xmlui/handle/123456789/2822, 90 pages.
Crumrine, P. K., "Management of Seizures in Lennox-Gastaut Syndrome," Pediatr Drugs, 13(2):107-118 (2011).
Curatolo, P. et al., "Management of epilepsy associated with tuberous sclerosis complex (TSC): Clinical recommendations," European Journal of Paediatric Neurology, 16:582-586 (2012).
Curia et al., "The pilocarpine model of temporal lobe epilepsy," J Neuroscience Methods, 172(2-4):143-157 (2008).
De Deyn et al., "Chemical models of epilepsy with some reference to their applicability in the development of anticonvulsants," Epilepsy Research, 12:87-110 (1992).
Depakene (valproic acid) capsules and oral solution, CV, Prescribing Information, 1978, 54 pages; https://www.accessdata.fda.gov/drugsatfda_docs/label/2013/018081s056lbl.pdf.
DeRosa et al., "Chapter XI: Epilepsy," Significant Pharmaceuticals Reported in US Patents, 1st Edition, May 2007, 10 pages.
Deshpande, et al., "Cannabinoid CB 1 receptor antagonists cause status epilepticus-like activity in the hippocampal neuronal culture model of acquired epilepsy," Neurosci Lett., 41 I(I):1-6 (2007). Epub Nov. 15, 2006.

De Meijer, "The Chemical Phenotypes (Chemotypes) of Cannabis," Chapter 5, Handbook of Cannabis, ed. Roger G. Pertwee, pp. 89-110 (2014).
Devinsky, Orrin, M.D. of the Department of Neurology for NYU Langone School of Medicine presents his talk on "Cannabidiols: A Brief History," at NYU School of Medicine's Cannabidiol Conference (Oct. 4, 2013). Video published online. <http://faces.med.nyu.edu/research-education/cannabidiol-conference>, 16 pages.
|Devinsky et al., "Epidiolex (Cannabidiol) in Treatment Resistant Epilepsy," Apr. 2015; https://epilepsyontario.org/wp-content/uploads/2015/Epidiolex-Cannabidiol-in-Treatment-Resistant-EpilepsyAAN-POSTER08Apr2015.pdf, 1 page.
Devinsky et al., "Efficacy and safety of Epidiolex (cannabidiol) in children and young adults with treatment-resistant epilepsy: Initial data from expanded access program," Jan. 2015, 2 pages.
Devinsky et al., "Cannabidiol in patients with treatment-resistant epilepsy: an open-label interventional trial," Lancet Neurology, 15(3):270-278 (2015).
|Devinsky et al., "Cannabidiol (CBD) significantly reduces drop seizure frequency in Lennox-Gastaut syndrome (LGS): results of a dose-ranging, multi-center, randomized, double-blind, placebo-controlled trial (GWPCARE3)," Epilepsia, 58:S13-S14 (2017), 2 pages.
|Devinsky et al., "Trial of Cannabidiol for Drug-Resistant Seizures in the Dravet Syndrome," N Engl J Med, 376(21):2011-2020 (2017).
Devinsky et al., "Cannabidiol efficacy independent of clobazam: Meta-analysis of four randomized controlled trials," Acta Neurol Scand., 142:531-540 (2020).
DIACOMIT™ Product Monograph, Submission Control 142417, Date of Preparation, Dec. 19, 2012, 37 pages.
Dilantin-125®, NDA 08762 Dilantin-125 (Phenytoin Oral Suspension, USP) FDA Approved Labeling Text dated Feb. 2013, 15 pages.
Di Marzo, Vincenzo, Ph.D. of the Endocannabinoid Research Group Istituto di Chimica Biomolecolare, Consiglio Nazionale delle Ricerche, Pozzuoli, Napoli, Italy presents his talk on "Cannabinoid Pharmacology & Mechanism of Action," at NYU School of Medicine's Cannabidiol Conference (Oct. 4, 2013). Video published online. < http://faces.med.nyu.edu/research-education/cannabidiol-conference>, 32 pages.
DiMarzo, V., Declaration Under 37 C.F.R. 1.132, dated Aug. 24, 2017, 21 pages.
Dos Santos, R. G. et al., "Phytocannabinoids and epilepsy," Journal of Clinical Pharmacy and Therapeutics, 40:135-143 (2015).
Epilepsy Patients Flock to Colorado after Medical Pot Gives Them Hope, Nov. 18, 2013, CBS Colorado News, 4 pages.
Elsohly, M. & Gul, W., "Chemical constituents of marijuana: The complex mixture of natural cannabinoids," Life Sciences, 78:539-548 (2005).
EPIDYOLEX 100 mg oral soluction, Summary of Product Characteristics, European Medicines Compendium, Sep. 2019, 19 pages; https://web.archive.org/web/20200920022105/https://www.medicines.org.uk/emc/product/10781/smpc.
Evans, Randolph W., Neurology Case Studies, Neurol Clin 24, xi-xii, 2006, 2 pages.
Fabiano, V. et al., "Adverse drug reactions in newborns, infants and toddlers: pediatric pharmacovigilance between present and future," Expert Opinion on Drug Safety, 11(1): 95-105 (2011); doi: 10.1517/14740338.2011.584531.
FDA, "Warning Letters and Test Results for Cannabidiol-Related Products," 2016 Warning Letters, 4 pages.
FDA, "Warning Letters and Test Results for Cannabidiol-Related Products," 2015 Warning Letters, 4 pages.
FDA, Guidance for Industry: Estimating the maximum Safe Starting Dose in Initial Clinical Trials for Therapeutics in Adult Healthy Volunteers, U.S. Dept of Health and Human Services: Food and Drug Administration, Jul. 2005, 30 pages.
FDA's Guidance for Industry Q3A Impurities in New Drug Substances, Revision 2, Jun. 2008, 17 pages.
FDA Guidance for Industry: Botanical Drug Development, U.S. Dept. of Health and Human Services: Food and Drug Administration, Dec. 2016, 34 pages.

(56) References Cited

OTHER PUBLICATIONS

FDA Guidance for Industry: Q11 Development and Manufacture of Drug Substances, U.S. Dept. of Health and Human Services: Food and Drug Administration, Nov. 2012, 36 pages.
FDA Guideline for Submitting Supporting Documentation in Drug Applications for the Manufacture of Drug Substances, published in 1987, 20 pages.
FDA Good Review Practice: Clinical Review of Investigational New Drug Applications, Office of New Drugs in the Center for Drug Evaluation and Research at the Food and Drug Administration, Dec. 2013, 113 pages.
FDA Guidance for Industry on Drug-Induced Liver Injury: Premarketing Clinical Evaluation, Food and Drug Administration, Jul. 30, 2009, 4 pages.
Fernandez-Ruiz, J. et al., "Cannabidiol for neurodegenerative disorders: important new clinical applications for this phytocannabinoid?" British Journal of Pharmacology, 75(2):323-333 (2012).
Flatow, N., "How Medical Marijuana Is Giving a Six-Year-Old Boy New Life," Sep. 18, 2012, 2 pages; https://archive.thinkprogress.org/how-medical-marijuana-is-giving-a-six-year-old-boy-new-life-b5a486fb1d48/.
Fryar, C. D. et al., Anthropometric reference data for children and adults: United States, 2011-2014, National Center for Health Statistics. Vital Health Statistics, 3(39), 2016, 46 pages.
French, Jacqueline A., M.D. Professor of Neurology at the NYU Epilepsy Center presents her talk on "Trials for Disease Modifying Therapies in Epilepsy," at NYU School of Medicine's Cannabidiol Conference (Oct. 4, 2013). Video published online. <http://faces.med.nyu.edu/research-education/cannabidiol-conference>, 22 pages.
|French, J. A. et al., "Adjunctive everolimus therapy for treatment-resistant focal-onset seizures associated with tuberous sclerosis (EXIST-3): a phase 3, randomised, double-blind, placebo-controlled study," Lancet, 388:2153-2163 (2016).
Friedman, Daniel, M.D. Assistant Professor of Neurology at the NYU Comprehensive Epilepsy Center presents his talk on "Pharmacology of CBD in Humans," at NYU School of Medicine's Cannabidiol Conference (Oct. 4, 2013). Video published online. < http://faces.med.nyu.edu/research-education/cannabidiol-conference>, 14 pages.
Gaoni, Y. & Mechoulam, R., "The Isolation and Structure of Δ1-Tetrahydrocannabinol and Other Neutral Cannabinoids from Hashish," J Am Chem Soc. Jan. 1, 19713;93(1):217-24. doi: 10.1021/ja00730a036.
Gaoni, Y. & Mechoulam, R., "Isolation, Structure, and Partial Synthesis of an Active Constituent of Hashish," J. Am. Chem. Soc. 1964, 86, 8, 1646-1647.
Garde, D., "Gw Pharmaceuticals Announces Physician Reports of Epidiolex Treatment Effect in Children and Young Adults With Treatment-Resistant Epilepsy From Physician-Led Expanded Access Treatment Program," Jun. 17, 2014, 4 pages; https://www.fiercebiotech.com/biotech/gw-pharmaceuticals-announces-physician-reports-of-epidiolex-r-treatment-effect-children-and.
Gaston, T. E. et al., "Quality of life in adults enrolled in an open-label study of cannabidiol (CBD) for treatment-resistant epilepsy," Epilepsy & Behavior, 95:10-17 (2019).
Gaston, T. E. et al., "Cannabis for the Treatment of Epilepsy: an Update," Curr Neurol Neurosci Rep., 18(11):73 (2018), 9 pages; doi: 10.1007/s11910-018-0882-y.
Gauthier et al., "Clobazam: A Safe, Efficacious, and Newly Rediscovered Therapeutic for Epilepsy," CNS Neurosci Ther., 21(7):543-548 (2015); doi: 10.1111/cns.12399. Epub Apr. 28, 2015.
Gedde, Retrospective Case Review of High CBD, Low THC Cannabis Extract (Realm Oil) for Intractable Seizure Disorders, 2013 Realm of Caring Foundation, 4 pages.
Gedde et al., "Whole Cannabis Extract of High Concentration Cannabidiol May Calm Seizures in Highly Refractory Pediatric Epilepsies," American Epilepsy Society, Dec. 2013, pp. 449-1450. Abstract.
Gedde & Maa "Whole Cannabis Extract of High Concentration Cannabidiol May Calm Seizures in Highly Refractory Pediatric Epilepsies," American Epilepsy Society, 67th Annual Meeting, Dec. 6-10, 2013. Abstract.
Geffrey, A. et al., "Cannabidiol (CBD) Treatment for Refractory Epilepsy in Tuberous Sclerosis Complex (TSC)," Dec. 4, 2014; www.aesnet.org, Abstract 2.427, 2 pages.
Geffrey et al., "Drug-drug interaction between clobazam and cannabidiol in children with refractory epilepsy," Epilepsia, 56(8):1246-1251 (2015).
Gemmill, R. M. et al., "Synergistic growth inhibition by Iressa and Rapaymycin is modulated by VHL mutations in renal cell carcinoma," British Journal of Cancer, 92:2266-2277 (2005).
Gillen, D., "How Does Caffeine Affect CBD?", Apr. 21, 2019, available at: https://web.archive.org/web/20191220210719/https://greendoorcbd.com/blogs/news/how-does-caffeine-affect-cbd, 4 pages.
Gloss, D. & Vickrey, B., "Cannabinoids for epilepsy (Review)," Cochrane Database of Systematic Reviews 2014, Issue 3. Art. No.: CD009270, 9 pages; DOI: 10.1002/14651858.CD009270.pub3.
Goldenberg, M. M., "Overview of Drugs Used For Epilepsy and Seizures," P & T, 35(7):392-415 (2010).
Greaves et al., "First Dose of Potential New Medicines to Humans: How Animals Help," Nature Reviews Drug Discovery, 3:226-236 (2004).
Green Roads CBD Coffee and Tea, Product Page, 2023, 5 pages; https://greenroads.com/collections/cbd-tea-cbd-coffee?nfsn=2488702.aa938d.
Grotenhermen et al., "The Therapeutic Potential of Cannabis and Cannabinoids," Dtsch Arztebl Int, 109(29-30): 495-501 (2012); doi:10.3238/arztebl.2012.0495.
Gunning et al., "Cannabidiol in conjunction with clobazam: analysis of four randomized controlled trials," Acta Neurol Scand., 143:154-163 (2021).
Goodman & Gilman, The Pharmacological Basis of Therapeutics (Brunton, Laurence L.; Lazo, John S.; Parker, Keith, eds. (2006); New York: McGraw-Hill. ISBN 0-07-142280-3); Chapter 19, Pharmacotherapy of the Epilepsies, 28 pages.
Gupta Video 2013, Weed—CNN Special; https://www.youtube.com/watch?v=Z3lMflQ_K6U.
Gupta, S., "Why I changed my mind on weed," Aug. 8, 2013; https://www.cnn.com/2013/08/08/health/gupta-changed-mind-marijuana/index.html, 8 pages.
GWPharm [online], "Orphan Drug Designation Granted for Epidiolex in Dravet syndrome by the FDA—Seven Expanded Access INDs granted by FDA to US physicians to treat with Epidiolex 125 children suffering from intractable epilepsy syndromes," GW Pharmaceuticals Press Release, Nov. 15, 2013, 5 pages.
GWPharm [online], "GW Pharmaceuticals Announces Preliminary Results of Phase 2a Study for its Pipeline Compound GWP42006," GW Pharmaceuticals Press Release, Feb. 21, 2018, 5 pages.
Ha et al., "Epilepsy: Treatment and Management," US Pharm., 38(1):35-39 (2013).
Haller, S. & Carroll, I., "Medical marijuana for kids? Some praise results while others worry about risks," Jul. 9, 2013, 3 pages; https://www.nbcnews.com/healthmain/medical-marijuana-kids-some-praise-results-while-others-worry-about-6c10506407.
Hancock, E. C. & Cross, J. H., "Treatment of Lennox-Gastaut syndrome (Review)," Cochrane Database of Systematic Reviews, 2013, Issue 2. Art. No.: CD003277, doi: 10.1002/14651858.CD003277.pub3., 35 pages.
Hanus et al., "Phyto-cannabinoids: a unified critical inventory," Review Article, Natural Product Reports; Royal Society of Chemistry, vol. 33, No. 12, Dec. 2016, pp. 1347, 1448, 37 pages.
Hazenkamp, A. et al., "Quantitative Analysis of Cannabinoids from *Cannabis sativa* Using H-NMR," Chem. Pharm. Bull., 52(6):718-721 (2004).
Hazenkamp, A., "Cannabis; extracting the medicine," Doctoral Thesis, 1976, Proefschrift Universiteit Leiden; https://extractionmagazine.com/wp-content/uploads/2018/06/Cannabis-extracting-the-medicine-Arno-Hazekamp-Thesis.pdf, 187 pages.
Hefler, J., "Parents of epileptic N.J. tot lament medical marijuana delays," The Philadelphia Enquirer, Jun. 22, 2013, 5 pages; https://

(56) References Cited

OTHER PUBLICATIONS www.inquirer.com/philly/health/20130623_Parents_of_epileptic_N_J_tot_lament_medical_marijuana_delays.html.

Hegde, M. et al., "Seizure exacerbation in two patients with focal epilepsy following marijuana cessation," Epilepsy & Behavior, 25:563-566 (2012).

Herlopian, A. et al., "Cannabidiol in treatment of refractory epileptic spasms: An open label study," Epilepsy & Behavior, 106:106988 (2020), 7 pages; https://doi.org/10.1016/j.yebeh.2020.106988.

Hess et al., "Cannabidiol as a new treatment for drug-resistant epilepsy in tuberous sclerosis complex," Epilepsia, 57(10):1617-1624 (2016).

Hill et al., "Cannabidivarin is anticonvulsant in mouse and rat," Br. J Pharmacol, 167(8):1629-1642 (2012).

Hill, A. J. et al., "Phytocannabinoids as novel therapeutic agents in CNS disorders," Pharmacology & Therapeutics, 133:79-97 (2012).

Hillig, K. W. & Mahlberg, P. G., "A chemotaxonomic analysis of cannabinoid variation in Cannabis (Cannabaceae)," American Journal of Botany, 91(6):966-975 (2004).

Holmes, G. L. et al., "Tuberous Sclerosis Complex and Epilepsy: Recent Developments and Future Challenges," Epilepsia, 48(4):617-630, 2007.

Hussain et al., "Perceived efficacy of cannabidiol-enriched cannabis extracts for treatment of pediatric epilepsy: A potential role for infantile spasms and Lennox-Gastaut syndrome," Epilepsy & Behavior, 47:138-141 (2015).

ILEGAL Trailer, YouTube video, Mar. 27, 2014; https://www.youtube.com/watch?v=CtJJ1pzMKxs, 5 pages.

INSYS Therapeutics Submits Drug Master File For Cannabidiol Active Pharmaceutical Ingredient (API), Marketwired, May 29, 2014; https://www.biospace.com/article/releases/insys-therapeutics-submits-drug-master-file-for-cannabidiol-active-pharmaceutical-ingredient-api-/, 5 pages.

INSYS Therapeutics Commences Dosing in Phase 1/2 Safety and Pharmacokinetic Study of Cannabidiol Oral Solution in Pediatric Epilepsy Patients, BioSpace(Apr. 23, 2015); https://www.biospace.com/article/releases/insys-therapeutics-commences-dosing-in-phase-1-2-safety-and-pharmacokinetic-study-of-cannabidiol-oral-solution-in-pediatricepilepsy-patients-/, 3 pages.

INSYS Therapeutics, Inc., Quarterly Report Form Q-10, U.S. Securities and Exchange Commission, Mar. 31, 2014; insy20140331_10q.htm, 42 pages.

INSYS Therapeutics, Inc., Corporate Integrity Agreement and Conditional Exclusion Release, 2014, 100 pages.

Jacobson, C., "Treating Epilepsy with Pharmaceutical-Grade CBD", Cannabis Science Today, Podcast, 2023, transcript timeline 4 pages; https://agriculturalgenomics.com/podcast/season1/treating-epilepsy-with-pharmaceutical-grade-cbd/.

Jiang, R. et al., "Cannabidiol Is a Potent Inhibitor of the Catalytic Activity of Cytochrome P450 2019," Drug Metab. Pharmacokinet., 28(4):332-338 (2013).

Jones et al., "Cannabidiol Displays Antiepileptiform and Antiseizure Properties in Vitro and in Vivo," J Pharmacol Exp Ther., 332(2):559-577 (2010).

Jones, N. A. et al., "Cannabidiol exerts anti-convulsant effects in animal models of temporal lobe and partial seizures," Seizure, 21:344-352 (2012).

Jones, P. G. et al., "Cannabidiol," Acta Cryst., B33:3211-3214 (1977).

Jutras-Aswad, Didier, M.D., M.S. of the Department of Psychiatry for the University of Montreal presents his talk on "CBD in Animal Models and Human Trials of Opiate Abuse," at NYU School of Medicine's Cannabidiol Conference (Oct. 4, 2013), 25 pages; Video published online. <http://faces.med.nyu.edu/research-education/cannabidiol-conference>.

Kalenderoglou et al., "Cannabidiol Reduces Leukemic Cell Size—But Is It Important?," Front. Pharmacol., Mar. 24, 2017, Sec. Ethnopharmacology, vol. 8—2017, 9 pages; https://doi.org/10.3389/fphar.2017.00144.

Karler et al., "The anticonvulsant activity of cannabidiol and cannabinol," Life Science, 13:1527-1531 (1973).

Kalepu, S. et al., "Oral lipid-based drug delivery systems—an overview," Acta Pharmaceutica Sinica B., 3(6):361-372 (2013).

Kassai et al., "Severe Myoclonic epilepsy in Infancy: A Systematic Review and a Meta-Analysis of Individual Patient Data," Epilepsia, 49(2):343-348 (2008).

Katz, Russell ("Rusty"), M.D. former Director of the Division of Neurology Products at the FDA presents his talk on "Dravet and Lennox-Gastaut Syndromes: The Orphan Drug Process," at NYU School of Medicine's Cannabidiol Conference (Oct. 4, 2013). Video published online. <http://faces.med.nyu.edu/research-education/cannabidiol-conference>, 25 pages.

Kerr, D. N. S. & Pillai, P. M., "Clobazam as adjunctive treatment in refractory epilepsy," British Medical Journal, 286:1246-1247 (1983).

Kobayashi T., et al., "Renal Carcinogenesis, Hepatic Hemangiomatosis and Embryonic Lethality Caused by a Germ-Line Tsc2 Mutation in Mice," Cancer Research, 59:1206-1211 (1999).

Koek et al., "Treatment-refractory posttraumatic stress disorder (TRPTSD): a review and framework for the future," Progress in Neuro-Psychopharmacology & Biological Psychiatry, 70:170-218 (2016).

Kopka, M., "Cannabinoids in the treatment of epilepsy—an updated review," Journal of Epileptology, 2019, 27:35-42; 10.21307/jepil-2019-004.

Krasowski, M. D., "Antiepileptic Drugs. Therapeutic Drug Monitoring of the Newer Generation Drugs," Jun. 2013, Clinical Laboratory News, https://www.aacc.org/cln/articles/2013/june/antiepileptic-drugs, 6 pages.

Kruk-Slomka et al., "A comparison of mecamylamine and bupropion effects on memory-related responses induced by nicotine and scopolamine in the novel object recognition test in mice," Pharmacological Reports, 66(4):638-646 (2014).

Kurz & Blass, "Use of dronabinol (delta-9-THC) in autism: A prospective single-case-study with an early infantile autistic child," Cannabinoids, 5(4):4-6 (2010).

LaPrarie et al., "Cannabidiol is a negative allosteric modulator of the cannabinoid CB1 receptor," British J Pharmacology, 172(20):4790-4805 (2015).

Leahy, J. T. et al., "Clobazam as an adjunctive therapy in treating seizures associated with Lennox-Gastaut syndrome," Neuropsychiatric Disease and Treatment, 7:673-681 (2011).

Leite et al., "New insights from the use of pilocarpine and kainate models," Epilepsy Research, 50:93-103 (2002).

Leo et al., "Antiepileptogenic effects of Ethosuximide and Levetiracetam in WAG/Rij rats are only temporary," Pharmacological Reports, 71:833-838 (2019).

Leo et al., "Cognitive impairment in the WAG/Rij rat absence model is secondary to absence seizures and depressive-like behavior," Progress in Neuropsychopharmacology & Biological Psychiatry, 94:109652 (2019), 16 pages.

Leonard, B. E., "Therapeutic Uses of Cannabis," British Medical Association (BMA). Harwood Academic Publishers, UK. 1997, pp. 592.

Lewis et al., "Chemical Profiling of Medical Cannabis Extracts," ACS Omega, 2:6091-6103 (2017).

Lodzki et al., "Cannabidiol—transdermal delivery and anti-inflammatory effect in a murine model," Journal of Controlled Release, 93:377-387 (2003).

Loscher, W. & Rogawski, M. A., "How theories evolved concerning the mechanism of action of barbiturates," Epilepsia, 53(Suppl. 8):12-25, 2012; doi: 10.1111/epi.12025.

Marks, W. J. et al., "Management of Seizures and Epilepsy," Am Fam Physician. 1998;57(7):1589-1600.

Malamut, M., "I Drank CBD Coffee for a Week. Here's What I Did to My Anxiety," Nov. 18, 2019, available at https://www.healthline.com/health/mental-health/i-tried-it-cbd-coffee-anxiety, 16 pages.

MARINOL® Product Description, NDA 18-651/S-025 and S-026, Jul. 2006, pp. 3-13.

Masangkay, E. G., "FDA Confirms GW Pharmaceuticals' IND For Epidiolex Trial In Dravet Syndrome," May 9, 2014; https://www.bioprocessonline.com/doc/fda-confirms-gw-pharmaceuticals-ind-for-epidiolex-trial-in-dravet-syndrome-0001, 2 pages.

(56) References Cited

OTHER PUBLICATIONS

Mead et al., "The Untold Story of the Cannabidiol (CBD) Revolution," US Neurology, 2018; 14(Suppl. 3):2-8. Published Online: Oct. 16, 2018.
Mechoulam, et al., "Toward drugs derived from cannabis," Naturwissenschaften, 65(4):174-9 (1978).
Mechoulam, R. et al., "Cannabidiol—Recent Advances," Chemistry & Biodiversity, vol. 4, pp. 1678-1692 (2007).
Mechoulam, R., "Conversation with Ralph Mechoulam," Addiction Jun. 2007;102(6):887-93. doi: 10.1111/j.1360-0443.2007.01795.x..
Mechoulam, R. & Parker, L. A., "The Endocannabinoid System and the Brain," Annu. Rev. Psychol. 2013. 64:21-47.
Mechoulam, R. & Parker, L. A., "Towards a better cannabis drug," British Journal of Pharmacology (2013) 170 1363-1364.
Mechoulam et al., "Cannabidiol: an overview of some chemical and pharmacological aspects. Part I: chemical aspects," Chemistry and Physics of Lipids, 121:35-43 (2002).
Mechoulam et al., "Hashish-I: The Structure of Cannabidiol," Tetrahedron, 19:2073-2078 (1963).
Montenegro et al., "Efficacy of Clobazam as Add-on Therapy for Refractory Epilepsy: Experience at a US Epilepsy Center," Clinical Neuropharmacology, 31(6):333-338 (2008).
Montouris, "Rational approach to treatment options for Lennox-Gastaut syndrome," Epilepsia, 52:10-20 (2011).
Moore, Y. et al., "Cannabidiol reduced frequency of convulsive seizures in drug resistant Dravet Syndrome," Structured Abstracts of Sentinel Articles: Picket, first published Sep. 22, 2017, reported in Arch Dis Child Educ Pract Ed Oct. 2018, vol. 103, No. 5., 2 pages. Abstract.
Morrison et al., "A Phase 1, Open-Label, Pharmacokinetic Trial to Investigate Possible Drug-Drug Interactions Between Clobazam, Stiripentol, or Valproate and Cannabidiol in Healthy Subjects," Clinical Pharmacology in Drug Development, 8(8):1009-1031 (2019).
Mudigoudar et al., "Emerging Antiepileptic Drugs for Severe Pediatric Epilepsies," Semin Pediatr Neurol, 23:167-179 (2016).
Nair et al., "A simple practice guide for dose conversion between animals and human," Journal of Basic and Clinical Pharmacy, 7:27-31 (2016).
New Drug Application No. 210365 for Epidiolex (cannabidiol) 100 mg/ml oral solution, Jun. 25, 2018, 12 pages.
[No Author Listed], The Reuters Staff, BRIEF-GW Pharma receives FDA fast-track designation for Dravet syndrome treatment, Jun. 6, 2014, 1 page; https://www.reuters.com/article/gwpharmaceuticals-brief/brief-gw-pharma-receives-fda-fast-track-designation-for-dravet-syndrome-treatment-idUSFWNOOL01D20140606.
[No Author Listed], "Medical Cannabis Community Wants To Remain Apart," Medical Marijuana News, Apr. 3, 2013, 3 pages; Kitsap Peninsula Business Journal, available at: https://www.420magazine.com/community/threads/medical-cannabis-community-wants-to-remain-apart.186955/.
ONFI™ (clobazam) tablets Prescribing Information, NDA 202067 Onfi (clobazam) Tablets for oral use FDA Approved Labeling Text, dated Oct. 21, 2011, 28 pages.
Oguni, H. et al., "Long-Term Prognosis of Lennox-Gastaut Syndrome," Epilepsia, 37(Suppl 3):44-47 (1996).
Oguni, H. et al., "Severe myoclonic epilepsy in infants—a review based on the Tokyo women's Medical University series of 84 cases," Brain Dev., 23:736-748 (2010).
Ostendorf, A. P. & Ng, Y-T., "Treatment-resistant Lennox-Gastaut syndrome: therapeutic trends, challenges and future directions," Neuropsychiatric Disease and Treatment, 13:1131-1140 (2017).
Palmer, A. C. et al., "Combination Cancer Therapy Can Confer Benefit via Patient-to-Patient Variability without Drug Additivity or Synergy," Cell, 171:1678-1691 (2017).
Panikasiwill, D. et al., "An endogenous cannabinoid (2-AG) is neuroprotective after brain injury," Nature 413:527-531 (2001).
Pellicia, et al., International Association for Cannabis as Medicine, IACM 3rd Conference on Cannabinoids in Medicine, Sep. 9-10, 2005, 2005 Conference on Cannabinoids in Medicine, 72 pages.

Perucca, "Cannabinoids in the Treatment of Epilepsy: Hard Evidence at Last?" Journal of Epilepsy Research, 7(2):61-76 (2017).
Pertwee, "Cannabidiol as a potential medicine," In: Mechoulam, R. (eds) Cannabinoids as Therapeutics. Milestones in Drug Therapy MDT (2005), pp. 47-65, Birkhäuser Basel. https://doi.org/10.1007/3-7643-7358-X_3.
Physician's Desk Reference, 63rd Ed., 2009, 423-461, 2192-2194, 2639-2242, 3019-3022.
Potter, C., "Cannabis Extract Brings Hope for Children with Epilepsy," Dec. 3, 2013, 3 pages.
"Pot or not? Why parents of kids with epilepsy want access to marijuana treatment," CTVNews.ca Staff, Published Thursday, Jul. 18, 2013; Last Updated Thursday, Jul. 18, 2013, 2 pages; https://www.ctvnews.ca/health/health-headlines/pot-or-not-why-parents-of-kids-with-epilepsy-want-access-to-marijuana-treatment-1.1372695?cache=.
Purcarin, G. & Ng, Y-T., "Experience in the use of clobazam in the treatment of Lennox-Gastaut syndrome," Ther Adv Neurol Disord 2014, vol. 7(3):169-176.
Ragona, F. et al., "Dravet syndrome: early clinical manifestations and cognitive outcome in 37 Italian patients," Brain Dev., 32:71-77 (2010).
Rison, R. A., "How to write a neurology case report," Journal of Medical Case Reports, 10:91 (2016); doi:10.1186/s13256-016-0867-x, 5 pages.
Rohrback, Brian G., Ph.D, MBA President of Infometrix, Inc. presents his talk on "Assays of Cannabinoids," at NYU School of Medicine's Cannabidiol Conference (Oct. 4, 2013). Video published online. <http://faces.med.nyu.edu/research-education/cannabidiol-conference>, 29 pages.
Romano et al., "Inhibition of colon carcinogenesis by a standardized Cannabis sativa extract with high content of cannabidiol," Phytomedicine, 21:631-639 (2014).
Rosenkrantz et al., "Inhalation, Parenteral and Oral LD50 Values of $\Delta^9$-Tetrahydrocannabinol in Fischer Rats," Toxicology and Applied Pharmacology, 28:18-27 (1974).
Rowe, R. C. et al., "Handbook of Pharmaceutical Excipients," Pharmaceutical Press and American Pharmacists Association 2009, pp. 17-19; https://www.academia.edu/16731682/Handbook_of_Pharmaceutical_Excipients_6th_Edition.
Russo et al., "Pharmacology of Epileptogenesis and Related Comorbidities in the WAG/Rij Rat Model of Genetic Absence Epilepsy," Journal of Neuroscience Methods, 310:54-62 (2018).
Russo et al., "Upholding WAG/Rij Rats as a Model of Absence Epileptogenesis: Hidden Mechanisms and a New Theory on Seizure Development," Neuroscience and Biobehavioral Reviews, 71:388-408 (2016).
Saade, D. & Joshi, C., "Pure Cannabidiol in the Treatment of Malignant Migrating Partial Seizures in Infancy: A Case Report," Pediatric Neurology, 52:544-547 (2015); http://dx.doi.org/10.1016/j.pediatrneurol.2015.02.008.
Samanta, D., "Cannabidiol: A Review of Clinical Efficacy and Safety in Epilepsy," Pediatric Neurology, 96:24-29 (2019).
Samara et al., "Pharmacokinetics of Cannabidiol in Dogs," Drug Metabolism and Disposition, 16(3):469-472 (1988).
Sands, T. T. et al., "Long-Term Safety, Tolerability, and Efficacy of Cannabidiol in Children with Refractory Epilepsy: Results from an Expanded Access Program in the US," CNS Drugs, 33:47-60 (2019); https://doi.org/10.1007/s40263-018-0589-2.
Sarkisova et al., "The WAG/Rij Strain: A Genetic Animal Model of Absence Epilepsy with Comorbidity of Depression," Progress in Neuro-Psychopharmacology & Biological Psychiatry, 35 854-876 (2011).
Sasidharan, S. et al., "Extraction, Isolation and Characterization of Bioactive Compounds from Plants' Extracts," Afr J Tradit Complement Altern Med., 8(1):1-10 (2018).
Schafroth, M. A. et al., "Stereodivergent Total Synthesis of $\Delta^9$-Tetrahydrocannabinols," Angew. Chem. Int. Ed., 53:13898-13901 (2014).
Schafroth et al., "$\Delta^9$-cis-Tetrahydrocannabinol: Natural Occurrence, Chirality, and Pharmacology," Journal of Natural Products, 84:2502-2510 (2021).

(56) References Cited

OTHER PUBLICATIONS

Scheffer, I. E., "Diagnosis and long-term course of Dravet syndrome," Eur J of Paediatric Neurology 16 (2012) S5-S8.
Schwieterman, M. L. et al., "Strawberry Flavor: Diverse Chemical Compositions, a Seasonal Influence, and Effects on Sensory Perception," PLoS ONE, 9(2): e88446 (2014); doi: 10.1371/journal.pone.0088446, 12 pages.
Screenshot confirming date of Epidiolex (Cannabidiol) in Treatment Resistant Epilepsy, Apr. 2015; https://epilepsyontario.org/wp-content/uploads/2015/Epidiolex-Cannabidiol-in-Treatment-Resistant-EpilepsyAAN-POSTER08Apr2015.pdf, 1 page.
Serra I., et al., "Cannabidiol modulates phosphorylated rpS6 signalling in a zebrafish model of Tuberous Sclerosis Complex," Behavioural Brain Research, 363:135-144 (2019).
Silva, R. et al., "Clobazam as Add-on Therapy in Children with Epileptic Encephalopathy," Can. J. Neurol. Sci., 33:209-213 (2006).
Silvestro, S. et al., "Use of Cannabidiol in the Treatment of Epilepsy: Efficacy and Security in Clinical Trials," Molecules 2019, 24, 1459, 25 pages; doi:10.3390/molecules24081459.
Sirven et al., Finding the Best Dosage of Medication, Epilepsy Foundation (Mar. 19, 2014); https://www.epilepsy.com/treatment/medicines/finding-best-dosage, 11 pages.
Sluss, R. J., "Comparison of Artificial Flavors in Commercial Products and Actual Natural Flavor via Gas Chromatography Mass Spectroscopy Data." (2009). Electronic Theses and Dissertations. Paper, 1804; https://dc.etsu.edu/etd/1804, 72 pages.
Smith, R. M., "Identification of Butyl Cannabinoids in Marijuana," Journal of Forensic Sciences, 42:610-618 (1997).
Smith et al., "$\Delta^1$-3-cis-Tetrahydrocannabinol in Cannabis Sativa," Phytochemistry, 16:1088-1089 (1977).
Subduction Coffee + Hemp, Product p. 2023, 5 pages; https://subductioncoffee.com/?afmc=2j&utm_campaing=2j&utm_source=leaddyno&utm_medium=affiliate.
Sun et al., "Comparative study of organic solvent and water-soluble lipophilic extractives from wheat straw I: yield and chemical composition," J Wood Sci, 49:47-52 (2003).
Specchio, L. M. & Beghi, E., "Should Antiepileptic Drugs Be Withdrawn in Seizure-Free Patients?" CNS Drugs, 18(4):201-212 (2004).
Stewart, K., "Families migrating to Colorado for a medical marijuana miracle," Nov. 11, 2013, 8 pages; https://archive.sltrib.com/article.php?id=57052556&itype=CMSID.
Stewart, K., "University of Utah doctors: Say 'yes' to cannabis oil for kids," By Kirsten Stewart The Salt Lake Tribune, Nov. 13, 2013, 4 pages.
Stinchcomb, A. L. et al., "Human skin permeation of $\Delta^9$-tetrahydrocannabinol, cannabidiol and cannabinol," JPP 2004, 56: 291-297.
Thiel, E. A., "Managing Epilepsy in Tuberous Sclerosis Complex," J Child Neurol 2004; 19:680-686.
Young, S., "Marijuana stops child's severe seizures," CNN Health online, Aug. 7, 2013, 4 pages; https://www.cnn.com/2013/08/07/health/charlotte-child-medical-marijuana/index.html#:~:text=The%20first%20time%20Paige%20Figi,seizures%20stopped%20for%20seven%20days.&text=The%20marijuana%20strain%20Charlotte%20and,has%20been%20named%20after%20her.
Study NCT02224690—A Study to Investigate the Efficacy and Safety of Cannabidiol (*GWP42003-P; CBD*) As Adjunctive Treatment for Seizures Associated With Lennox-Gastaut Syndrome in Children and Adults, Aug. 22, 2014; https://clinicaltrials.gov/ct2/show/NCT02224690, 1 page.
Tanya Lewis, Mystery Mechanisms, The Scientist Magazine, Jul. 29, 2016, 2 pages; http://www.the-scientist.com/.
Thomas et al., "Cannabidiol displays unexpectedly high potency as an antagonist of CB1 and CB2 receptor agonists in vitro," British J Pharmacology, 150(5):613-623 (1988).
Thomas et al., "Characterization of the Lipophilicity of Natural and Synthetic Analogs of $\Delta^9$-Tetrahydrocannabinol and Its Relationship to Pharmacological Potency," The Journal of Pharmacology and Experimental Therapeutics, 255(2):624-630 (1990).
Thompson et al., "Comparison of acute oral toxicity of cannabinoids in rats, dogs and monkeys," Toxicology and Applied Pharmacology, vol. 25, Issue 3, pp. 363-372 (1973).
Thompson et al., "Oral and Intravenous Toxicity of $\Delta^9$-Tetrahydrocannabinol in Rheus Monkeys," Toxicology and Applied Pharmacology, 27:648-665 (1974).
Tose, L. V. et al., "Isomeric separation of cannabinoids by UPLC combined with ionic mobility mass spectrometry (TWIM-MS)—Part I," International Journal of Spectrometry, 418:112-121 (2016).
Trost, B. M. & Dogra, K., "Synthesis of (-)-$\Delta$9-trans-Tetrahydrocannabinol: Stereocontrol via Mo-Catalyzed Asymmetric Allylic Alkylation Reaction," Organic Letters, 9(5):861-863 (2007).
Turkanis et al., "Excitatory and Depressant Effects of Delta-9-Tetrahydrocannabidinol and Cannabidiol on Cortical Evoked Responses in the Conscious Rat," Psychopharmacology, 75:294-298 (1981).
Uliss et al., "The conversion of 3,4-CIS- to 3,4-TRANS-cannabinoids," Tetrahedron, 34:1885-1888 (1978).
"Marinol®," label retrieved from: <https://www.accessdata.fda.gov/dmgsatfda docs/label/2006/018651 s025s026lbl.pdf>, 11 pages.
Van Bakel et al., "The draft genome and transcriptome of *Cannabis sativa*," Genome Biology 2011, 12: R102, 18 pages; http://genomebiology.com/2011/12/10/R102 (Oct. 24, 2011).
Van Straten et al., "Update on the Management of Lennox-Gastaut Syndrome," Pediatric Neurology, 47:153-161 (2012).
Velisek, L., "Models of Chemically-Induced Acute Seizures," In Models of Seizures and Epilepsy, 127-152, 2006.
Vrielynck, P., "Current and emerging treatments for absence seizures in young patients," Neuropsychiatric Disease and Treatment, 9:963-975 (2013).
Warzak et al., "Caffeine Consumption in Young Children," The Journal of Pediatrics, vol. 158, Issue 3, P508-509, Mar. 1, 2011.
Weed Wars, Video I, Dec. 10, 2011, Weed Wars: The Story of Jayden-Andrew DeAngelo; https://www.youtube.com/watch?v=2WizdR5uHj0.
Weed Wars, Video II, May 25, 2013, 3 pages; available at https://www.youtube.com/watch?v=XBX_DB9sw5U.
WeedWars, CNN Special, Decriminialise It, Dr. Sanjay Gupta, 2013; https://www.youtube.com/watch?v=Z3lMfl1_K6U, 8 pages.
Weed Country, Episode 5, 2013; https://www.youtube.com/watch?v=0isjCcMtxBk; https://www.youtube.com/watch?v=GitMYGvwC4E&t=212s, 25 pages.
Weed Country, Episode 6, 2013; https://www.youtube.com/watch?v=Uyzuy1fNQfQ, 18 pages.
Nathaniel Morris (of Weed Country on Discovery Channel), Selected Media Examples of Pediatric Applications of Cannabidiol, 2013, 6 pages; available at https://www.youtube.com/watch?v=Mw3wiWkbRg8.
Whalley, Benjamin J. Ph.D. of the University of Reading presents his talk on "Cannabis and Epilepsy: Cannabidiol (CBD) and Cannabidavarin (CBDV) in Preclinical Models of Seizure and Epilepsy," at NYU School of Medicine's Cannabidiol Conference (Oct. 4, 2013). Video published online. <http://faces.med.nyu.edu/research-education/cannabidiol-conference>, 30 pages.
Wheless, J. W. et al., "Pharmacokinetics and Tolerability of Multiple Doses of Pharmaceutical-Grade Synthetic Cannabidiol in Pediatric Patients with Treatment-Resistant Epilepsy," CNS Drugs, 33(6):593-604 (2019); doi: 10.1007/s40263-019-00624-4.
[Anonymous] "When to Expect Results from CW Hemp Oil", downloaded Sep. 5, 2017, https://www.cwhemp.com/blog/expecting-results-from-hemp, 9 pages.
Whittle et al., (2001). Prospects for New Cannabis-Based Prescription Medicines. Journal of Cannabis Therapeutics. 1(3-4); doi:10.1300/J175v01, 1(3-4), 23 pages.
Wilkey, R., "'Weed Wars': Five-Year-Old Takes Medical Marijuana On Reality Show (VIDEO)", Dec. 10, 2011, 7 pages; https://www.huffpost.com/entry/weed-wars-five-year-old-smokes-marijuana_n_1140351.
Williams, "The Key to Healing Broken Bones May be Found in This Illegal Drug," Jul. 25, 2015; https://www.fool.com/investing/high-growth/2015/07/25/the-key-to-healing-broken-bones-may-be-found-in-th.aspx#:~:text=As%20published%20in%20the%20Journal,rats%20in%20just%20eight%20 weeks, 5 pages.

(56) References Cited

OTHER PUBLICATIONS

Willis, L., "Final Report on the Safety Assessment of Sesame Oil," Journal of the American College of Toxicology, 12(3):261-277 (1993).
Wright et al., Cannabidiol (CBD) in Dravet Syndrome: A Randomised, Dose-Ranging Pharmacokinetics and Safety Trial (GWPCARE1), Epilepsia, 58(Suppl. 5): S5-S199 (2017), p. 0240 Abstract, 1 page.
Zamberletti et al., "Alterations of prefrontal cortex GABAergic transmission in the complex psychotic-like phenotype induced by adolescent delta-9-tetrahydrocannabinol exposure in rats," Neurobiology of Disease, 63:35-47 (2014).
Zhang, T. et al., "Pre-seizure state identified by diffuse optical tomography," Scientific Reports, 4:3798 (2014); https://doi.org/10.1038/srep03798, 10 pages.
Zuardi et al., "Antipsychotic Effect of Cannabidiol," J Clin Psychiatry, 56(10):485-486 (1995).
Zuardi et al., "Cannabidiol for the treatment of psychosis in Parkinson's disease," Journal of Psychopharmacology, 23(8):979-983 (2009).
Zuardi A., et al., "Inverted U-Shaped Dose-Response Curve of the Anxiolytic Effect of Cannabidiol during Public Speaking in Real Life," Frontiers in Pharmacology, 8, Article 259, pp. 1-9 (2017).
U.S. Appl. No. 15/640,033, filed Jun. 30, 2017.
U.S. Appl. No. 16/959,354, filed Jun. 30, 2020.
U.S. Appl. No. 16/935,005, filed Jul. 21, 2020.
U.S. Appl. No. 17/012,448, filed Sep. 4, 2020.
U.S. Appl. No. 17/050,956, filed Oct. 27, 2020.
U.S. Appl. No. 17/102,109, filed Nov. 23, 2020.
U.S. Appl. No. 17/231,625, filed Apr. 15, 2021.
U.S. Appl. No. 17/296,066, filed May 21, 2021.
U.S. Appl. No. 17/296,076, filed May 21, 2021.
U.S. Appl. No. 17/424,682, filed Jul. 21, 2021.
U.S. Appl. No. 17/426,442, filed Jul. 28, 2021.
U.S. Appl. No. 17/406,401, filed Aug. 19, 2021.
U.S. Appl. No. 17/435,892, filed Sep. 2, 2021.
U.S. Appl. No. 17/606,370, filed Oct. 25, 2021.
U.S. Appl. No. 17/611,824, filed Nov. 16, 2021.
U.S. Appl. No. 17/548,232, filed Dec. 10, 2021.
U.S. Appl. No. 17/576,868, filed Jan. 14, 2022.
U.S. Appl. No. 17/627,946, filed Jan. 18, 2022.
U.S. Appl. No. 17/585,485, filed Jan. 26, 2022.
U.S. Appl. No. 17/631,069, filed Jan. 28, 2022.
U.S. Appl. No. 17/638,629, filed Feb. 25, 2022.
U.S. Appl. No. 17/689,607, filed Mar. 8, 2022.
U.S. Appl. No. 17/689,245, filed Mar. 8, 2022.
U.S. Appl. No. 17/768,048, filed Apr. 11, 2022.
U.S. Appl. No. 17/770,435, filed Apr. 20, 2022.
U.S. Appl. No. 17/770,436, filed Apr. 20, 2022.
U.S. Appl. No. 17/771,184, filed Apr. 22, 2022.
U.S. Appl. No. 17/771,190, filed Apr. 22, 2022.
U.S. Appl. No. 17/771,195, filed Apr. 22, 2022.
U.S. Appl. No. 17/771,183, filed Apr. 22, 2022.
U.S. Appl. No. 17/744,224, filed May 13, 2022.
U.S. Appl. No. 17/777,734, filed May 18, 2022.
U.S. Appl. No. 17/777,677, filed May 18, 2022.
U.S. Appl. No. 17/777,681, filed May 18, 2022.
U.S. Appl. No. 17/841,167, filed Jun. 15, 2022.
U.S. Appl. No. 17/786,949, filed Jun. 17, 2022.
U.S. Appl. No. 17/853,367, filed Jun. 29, 2022.
U.S. Appl. No. 17/817,753, filed Aug. 5, 2022.
U.S. Appl. No. 18/002,437, filed Dec. 19, 2022.
U.S. Appl. No. 18/005,838, filed Jan. 17, 2023.
U.S. Appl. No. 18/005,841, filed Jan. 17, 2023.
U.S. Appl. No. 18/005,843, filed Jan. 17, 2023.
U.S. Appl. No. 18/005,845, filed Jan. 17, 2023.
U.S. Appl. No. 18/005,847, filed Jan. 17, 2023.
U.S. Appl. No. 18/005,848, filed Jan. 17, 2023.
U.S. Appl. No. 18/005,851, filed Jan. 18, 2023.
U.S. Appl. No. 18/005,852, filed Jan. 18, 2023.
U.S. Appl. No. 18/005,853, filed Jan. 18, 2023.
U.S. Appl. No. 18/005,868, filed Jan. 18, 2023.
U.S. Appl. No. 18/005,959, filed Jan. 18, 2023.
U.S. Appl. No. 18/005,960, filed Jan. 18, 2023.
U.S. Appl. No. 18/005,961, filed Jan. 18, 2023.
U.S. Appl. No. 18/006,121, filed Jan. 19, 2023.
U.S. Appl. No. 18/006,125, filed Jan. 19, 2023.
U.S. Appl. No. 18/006,127, filed Jan. 19, 2023.
U.S. Appl. No. 18/006,129, filed Jan. 19, 2023.
U.S. Appl. No. 18,006,131, filed Jan. 19, 2023.
U.S. Appl. No. 18,006,133, filed Jan. 19, 2023.
U.S. Appl. No. 18/161,603, filed Jan. 30, 2023.
U.S. Appl. No. 18/170,235, filed Feb. 16, 2023.
U.S. Appl. No. 18/043,810, filed Mar. 2, 2023.
U.S. Appl. No. 18/044,941, filed Mar. 10, 2023.
U.S. Appl. No. 18/245,856, filed Mar. 17, 2023.
U.S. Appl. No. 18/186,792, filed Mar. 20, 2023.
U.S. Appl. No. 18/311,221, filed May 2, 2023.
U.S. Appl. No. 18/256,307, filed Jun. 7, 2023.
U.S. Appl. No. 18/257,373, filed Jun. 14, 2023.
U.S. Appl. No. 18/257,537, filed Jun. 14, 2023.
U.S. Appl. No. 18/257,479, filed Jun. 14, 2023.
U.S. Appl. No. 18/258,485, filed Jun. 20, 2023.
U.S. Appl. No. 18/446,405, filed Aug. 8, 2023.
U.S. Appl. No. 18/546,254, filed Aug. 11, 2023.
U.S. Appl. No. 18/548,003, filed Aug. 25, 2023.
U.S. Appl. No. 18/477,467, filed Sep. 28, 2023.
U.S. Appl. No. 18/479,671, filed Oct. 2, 2023.
U.S. Appl. No. 18/560,316, filed Nov. 10, 2023.
U.S. Appl. No. 18/560,337, filed Nov. 10, 2023.
U.S. Appl. No. 18/560,341, filed Nov. 10, 2023.
U.S. Appl. No. 18/560,346, filed Nov. 10, 2023.
U.S. Appl. No. 18/526,795, filed Dec. 1, 2023.
U.S. Appl. No. 18/545,754, filed Dec. 19, 2023.
U.S. Appl. No. 18/292,844, filed Jan. 26, 2024.
U.S. Appl. No. 18/597,717, filed Mar. 6, 2024.
Notice of Opposition to European Patent Application No. EP18737374.1, Patent No. EP3641819, dated Jul. 12, 2024, 23 pages.
Advagraf 0.5 mg prolonged-release hard capsules, Advagraf 1 mg prolonged-release hard capsules, Advagraf 3 mg prolonged-release hard capsules, Advagraf 5 mg prolonged-release hard capsules, Annex 1—Summary of Product Characteristics, retrieved on Aug. 13, 2024, 6 pages.
Devarbhavi, "An update on drug-induced liver injury," J. Clinical and Experimental Hepatology, 2(3):247-259 (2012.
Kelley, "Medical Cannabis Community Wants to Remain Apart," Kitsap Peninsula Business Journal, Apr. 3, 2013; available at https://www.420magazine.com/community/threads/medical-cannabis-community-wants-to-remain-apart.186955/, 4 pages.
KLONOPIN® Tablets (clonazepam) KLONOPIN® Wafers (clonazepam orally disintegrating tablets) Product Label, revised Apr. 4, 2009, 18 pages.
Rosenkrantz et al., "Toxicity of Short-Term Administration of Cannabinoids to Rhesus Monkeys," Toxicology and Applied Pharmacology, 58:118-131 (1981).
EPIDIOLEX® (cannabidiol) oral solution, CV, Prescribing Information, 2021, 38 pages; https://www.accessdata.fda.gov/drugsatfda_docs/label/2021/210365Orig1s011lbl.pdf.
EPIDIOLEX® (cannabidiol) oral solution, CV, Prescribing Information, 2024, 32 pages; https://pp.jazzpharma.com/pi/epidiolex.en.USPI.pdf.
Feierman, D. E. & Lasker, J. M., "Metabolism of fentanyl, a synthetic opioid analgesic, by human liver microsomes. Role of CYP3A4," Drug Metabolism and Disposition, 24(9):932-939, Sep. 1996, Abstract. https://dmd.aspetjournals.org/content/24/9/932, 4 pages.
Manini et al., "Safety and Safety and Pharmacokinetics of Oral Cannabidiol When Administered Concomitantly With Intravenous Fentanyl in Humans," J Addict Med., 9(3): 204-210 (2015); doi:10.1097/ADM.0000000000000118.
Morrison et al., "A Phase 1 Investigation Into the Potential Effects of Cannabidiol on CYP3A4-Mediated Drug-Drug Interactions in Healthy Volunteers," Abstract No. 1.297, Submission ID: 500033, Presentation Date: Dec. 1, 2018, Published Date: Nov. 5, 2018;

(56) References Cited

OTHER PUBLICATIONS https://aesnet.org/abstractslisting/a-phase-1-investigation-into-the-potential-effects-of-cannabidiol-on-cyp3a4-mediated-drug-drug-interactions-in-healthy-volunteers, 2 pages.

Patsalos et al., "Clinical implications of trials investigating drug-drug interactions between cannabidiol and enzyme inducers or inhibitors or common antiseizure drugs," Epilepsia, 61:1854-1868 (2020).

Notice of Opposition to European Patent Application No. EP19702670.1, Patent No. EP3743053, dated Aug. 27, 2024, 22 pages.

Actiq™ (Oral Transmucosal Fentanyl Citrate), Clinical Pharmacology and Biopharmaceutics Review, Reviewer Suresh Doddapaneni, Ph.D., Center for Drug Evaluation and Research, Application No. NDA 20747, Submission Date: Nov. 11, 1996, Review Date: Apr. 22, 1997, 25 pages.

Afternoon Session, Panel 1—Living with TSC and LAM, Offical Transcript (Part 3 of 4) of the Video "Externally-Led Patient-Focused Drug Development Meeting," Silver Springs, Maryland, Jun. 21, 2017, available on You Tube at https://www.youtube.com/watch?v=qoxOKR3WpFs, 24 pages.

Afternoon Session, Panel 2—Current and Future Approaches to Treating TSC and LAM, Offical Transcript (Part 4 of 4) of the Video "Externally-Led Patient-Focused Drug Development Meeting," Silver Springs, Maryland, Jun. 21, 2017, available on You Tube at https://www.youtube.com/watch?v=qoxOKR3WpFs, 17 pages.

[No Author Listed] The Voice of the Patient, A Report from the Tuberous Slerosis Alliance's Externally-Led Patient-Focused Drug Development Meeting, Report Date: Oct. 26, 2017, Public Meeting Jun. 21, 2017, 79 pages.

Conference Book of the 2017 International Research Conference on TSC and LAM: Innovating Through Partnerships, Washington, D.C., Jun. 22-24, 2017, 160 pages.

Devinsky et al., Trial Protocol, Supplementary Material to "Trial of Cannabidiol for Drug-Resistant Seizures in the Dravet Syndrome," N Engl J Med, 376(21):2011-2020 (2017), 426 pages.

Franz, D. N. & Capal, J. K., "mTOR inhibitors in the pharmacologic management of tuberous sclerosis complex and their potential role in other rare neurodevelopmental disorders," Orphanet Journal of Rare Diseases, 12:51 (2017), 9 pages; doi: 10.1186/s13023-017-0596-2.

Krueger et al., "Tuberous Sclerosis Complex Surveillance and Management: Recommendations of the 2012 International Sclerosis Complex Consensus Conference," Pediatric Neurology, 49:255-265 (2013).

Labroo et al., "Fentanyl metabolism by human hepatic and intestinal cytochrome P450 3A4: implications for interindividual variability in disposition, efficacy, and drug interactions," Drug Metab Dispos, 25(9):1072-80 (1997).

Morning Session, Panel 1—Living with TSC and LAM, Offical Transcript (Part 1 of 4) of the Video "Externally-Led Patient-Focused Drug Development Meeting," Silver Springs, Maryland, Jun. 21, 2017, available on You Tube at https://www.youtube.com/watch?v=qoxOKR3WpFs, 26 pages.

Morning Session, Panel 2—Current and Future Treatments for TSC, Offical Transcript (Part 2 of 4) of the Video "Externally-Led Patient-Focused Drug Development Meeting," Silver Springs, Maryland, Jun. 21, 2017, available on You Tube at https://www.youtube.com/watch?v=qoxOKR3WpFs, 19 pages.

Nazario et al., "Caffeine protects against memory loss induced by high and non-anxiolytic dose of cannabidiol in adult zebrafish (*Danio rerio*)," Pharmacol Biochem Behav, 135:210-6 (2015); doi: 10.1016/j.pbb.2015.06.008. Epub Jun. 20, 2015.

[No Author Listed], European Medicines Agency (EMA), "Public summary of opinion on orphan designation—Cannabidiol for the treatment of Dravet syndrome," Nov. 10, 2014, https://www.ema.europa.eu/en/documents/orphandesignation/eu3141339-public-summary-opinion-orphan-designation-cannabidiol-treatment-dravetsyndrome-en.pdf, 4 pages.

Peron, A. et al., Agenda Program and Description of the "2nd Early Tuberous Slerosis Complex Researcher Meeting," Washington, DC, Jun. 21, 2017, 6 pages.

Shrivastava et al., "Cannabidiol Induces Programmed Cell Death in Breast Cancer Cells by Coordinating the Cross-talk Between Apoptosis and Autophagy," Mol Cancer Ther; 10(7):1161-1172 (2011).

Vezyroglou, K. & Cross, J. H., "Targeted Treatment in Childhood Epilepsy Syndromes," Curr Treat Options Neurol, 18:29 (2016), Published online May 7, 2016. doi: 10.1007/s11940-016-0407-4, 12 pages.

Wirrell, E. C., "Treatment of Dravet Syndrome," Can J Neurol Sci., 43:S13-S18 (2016).

Cunetti, L. et al., "Chronic Pain Treatment with Cannabidiol in Kidney Transplant Patients in Uruguay," Transplantation Proceedings, vol. 30 (Suppl. 2): 390-576 (2017), 1 page.

Timmings et al., "Lamotrigine as an Add-On Drug in the Management of Lennox-Gastaut Syndrome," European Neurology, 32(6):305-307 (1992).

\* cited by examiner

USE OF CANNABINOIDS IN THE TREATMENT OF EPILEPSY

CROSS-REFERENCE TO RELATED APPLICATIONS

This application claims the benefit of International PCT Application No. PCT/GB2018/053483, filed Nov. 30, 2018; and Great Britain Application No. 1720020.5, filed Dec. 1, 2017; all of which are incorporated herein by reference to their entirety.

FIELD OF THE INVENTION

The present invention relates to the use of cannabidiol (CBD) in the treatment of patients with childhood-onset epilepsy who are concurrently taking immunosuppressant drugs.

In particular the immunosuppressant drug is a calcineurin inhibitor. More particularly the immunosuppressant drug is tacrolimus.

Where the CBD is used in combination with an immunosuppressant drug, caution should be taken. For example, the dose of either the CBD and/or the immunosuppressant drug may be required to be reduced. Moreover, the patient may need to be monitored for side effects of said drug-drug interaction.

Preferably the CBD used is in the form of a highly purified extract of cannabis such that the CBD is present at greater than 98% of the total extract (w/w) and the other components of the extract are characterised. In particular the cannabinoid tetrahydrocannabinol (THC) has been substantially removed, to a level of not more than 0.15% (w/w) and the propyl analogue of CBD, cannabidivarin, (CBDV) is present in amounts of up to 1%. Alternatively, the CBD may be a synthetically produced CBD.

BACKGROUND TO THE INVENTION

Epilepsy occurs in approximately 1% of the population worldwide, (Thurman et al., 2011) of which 70% are able to adequately control their symptoms with the available existing anti-epileptic drugs (AEDs). However, 30% of this patient group, (Eadie et al., 2012), are unable to obtain seizure freedom from the AED that are available and as such are termed as suffering from intractable or "treatment-resistant epilepsy" (TRE).

Intractable or treatment-resistant epilepsy was defined in 2009 by the International League Against Epilepsy (ILAE) as "failure of adequate trials of two tolerated and appropriately chosen and used AED schedules (whether as monotherapies or in combination) to achieve sustained seizure freedom" (Kwan et al., 2009).

Individuals who develop epilepsy during the first few years of life are often difficult to treat and as such are often termed treatment-resistant. Children who undergo frequent seizures in childhood are often left with neurological damage which can cause cognitive, behavioral and motor delays.

Childhood-onset epilepsy is a relatively common neurological disorder in children and young adults with a prevalence of approximately 700 per 100,000. This is twice the number of epileptic adults per population.

When a child or young adult presents with a seizure, investigations are normally undertaken in order to investigate the cause. Childhood epilepsy can be caused by many different syndromes and genetic mutations and as such diagnosis for these children may take some time.

The main symptom of epilepsy is repeated seizures. In order to determine the type of epilepsy or the epileptic syndrome that a patient is suffering from, an investigation into the type of seizures that the patient is experiencing is undertaken. Clinical observations and electroencephalography (EEG) tests are conducted and the type(s) of seizures are classified according to the ILAE classification described below.

The International classification of seizure types proposed by the ILAE was adopted in 1981 and a revised proposal was published by the ILAE in 2010 and has not yet superseded the 1981 classification. The 2010 proposal for revised terminology includes the proposed changes to replace the terminology of partial with focal. In addition, the term "simple partial seizure" has been replaced by the term "focal seizure where awareness/responsiveness is not impaired" and the term "complex partial seizure" has been replaced by the term "focal seizure where awareness/consciousness is impaired".

Generalised seizures, where the seizure arises within and rapidly engages bilaterally distributed networks, can be split into six subtypes: Tonic-Clonic (grand mal) seizures; Absence (petit mal) Seizures; Clonic Seizures; Tonic Seizures; Atonic Seizures and Myoclonic Seizures.

Focal (partial) seizures where the seizure originates within networks limited to only one hemisphere, are also split into sub-categories. Here the seizure is characterized according to one or more features of the seizure, including aura, motor, autonomic and awareness/responsiveness. Where a seizure begins as a localized seizure and rapidly evolves to be distributed within bilateral networks this seizure is known as a Bilateral convulsive seizure, which is the proposed terminology to replace Secondary Generalised Seizures (generalized seizures that have evolved from focal seizures and are no longer remain localized).

Epileptic syndromes often present with many different types of seizure and identifying the types of seizure that a patient is suffering from is important as many of the standard AEDs are targeted to treat or are only effective against a given seizure type/sub-type.

One such childhood epilepsy syndrome is Lennox-Gastaut syndrome (LGS). LGS is a severe form of epilepsy, where seizures usually begin before the age of 4. Seizure types, which vary among patients, include tonic (stiffening of the body, upward deviation of the eyes, dilation of the pupils, and altered respiratory patterns), atonic (brief loss of muscle tone and consciousness, causing abrupt falls), atypical absence (staring spells), and myoclonic (sudden muscle jerks). There may be periods of frequent seizures mixed with brief, relatively seizure-free periods.

Seizures in LGS are often described as "drop seizures". Such drop seizures are defined as an attack or spell (atonic, tonic or tonic-clonic) involving the entire body, trunk or head that led or could have led to a fall, injury, slumping in a chair or hitting the patient's head on a surface.

Most patients with LGS experience some degree of impaired intellectual functioning or information processing, along with developmental delays, and behavioural disturbances.

LGS can be caused by brain malformations, perinatal asphyxia, severe head injury, central nervous system infection and inherited degenerative or metabolic conditions. In 30-35% of cases, no cause can be found.

The first line treatment for drop seizures, including the treatment of drop seizures in patients with LGS, usually comprises a broad-spectrum AED, such as sodium valproate often in combination with rufinamide or lamotrigine. Other AEDs that may be considered include felbamate, clobazam and topiramate.

AEDs such as carbamezapine, gabapentin, oxcarbazepine, pregabalin, tiagabineor and vigabatrin are contraindicated in drop seizures.

Common AEDs defined by their mechanisms of action are described in the following tables:

TABLE 1

Examples of narrow spectrum AEDs

| Narrow-spectrum AED | Mechanism | Indication |
|---|---|---|
| Phenytoin | Sodium channel | Complex partial Tonic-clonic |
| Phenobarbital | GABA/Calcium channel | Partial seizures Tonic-clonic |
| Carbamazepine | Sodium channel | Partial seizures Tonic-clonic Mixed seizures |
| Oxcarbazepine | Sodium channel | Partial seizures Tonic-clonic Mixed seizures |
| Gabapentin | Calcium channel | Partial seizures Mixed seizures |
| Pregabalin | Calcium channel | Adjunct therapy for partial seizures with or without secondary generalisation |
| Lacosamide | Sodium channel | Adjunct therapy for partial seizures |
| Vigabatrin | GABA | Secondarily generalized tonic-clonic seizures Partial seizures Infantile spasms due to Wes tsyndrome |

TABLE 2

Examples of broad spectrum AEDs

| Broad-spectrum AED | Mechanism | Indication |
|---|---|---|
| Valproic acid | GABA/Sodium channel | First-line treatment for tonic-clonic seizures, absence seizures and myoclonic seizures Second-line treatment for partial seizures and infantile spasms. Intravenous use in status epilepticus |
| Lamotrigine | Sodium channel | Partial seizures Tonic-clonic Seizures associated with Lennox-Gastaut syndrome |
| Ethosuximide | Calcium channel | Absence seizures |
| Topiramate | GABA/Sodium channel | Seizures associated with Lennox-Gastaut syndrome |
| Zonisamide | GABA/Calcium/Sodium channel | Adjunctive therapy in adults with partial-onset seizures Infantile spasm Mixed seizure Lennox-Gastaut syndrome Myoclonic Generalised tonic-clonic seizure |
| Levetiracetam | Calcium channel | Partial seizures Adjunctive therapy for partial, myoclonic and tonic-clonic seizures |
| Clonazepam | GABA | Typical and atypical absences Infantile myoclonic Myoclonic seizures Akinetic seizures |

TABLE 2-continued

Examples of broad spectrum AEDs

| Broad-spectrum AED | Mechanism | Indication |
|---|---|---|
| Rufinamide | Sodium channel | Adjunctive treatment of partial seizures associated with Lennox-Gastaut syndrome |

TABLE 3

Examples of AEDs used specifically in childhood epilepsy

| AED | Mechanism | Indication |
|---|---|---|
| Clobazam | GABA | Adjunctive therapy in complex partial seizures Status epilepticus Myoclonic Myoclonic-absent Simple partial Complex partial Absence seizures Lennox-Gastaut syndrome |
| Stiripentol | GABA | Severe myoclonic epilepsy in infancy (Dravet syndrome) |

The present invention describes surprising data from a patient that was taking an immunosuppressant drug, tacrolimus during the open label extension part of a clinical trial into childhood-onset epilepsy.

It was noted that there was a significant increase in the subjects blood urea nitrogen (BUN) and serum creatine levels during the time the subject was taking CBD. Such an interaction is unexpected and as such the use of these drugs in combination should be done with close monitoring of the patient.

BRIEF SUMMARY OF THE DISCLOSURE

In accordance with a first aspect of the present invention there is provided cannabidiol (CBD) for use in the treatment of childhood-onset epilepsy in patients who are concurrently taking an immunosuppressant drug characterised in that the blood levels of the immunosuppressant drug and associated markers are monitored to ensure the levels do not become toxic.

Preferably the dose of CBD is lowered. Alternatively the dose of the immunosuppressant drug is lowered.

Preferably the immunosuppressant drug is tacrolimus.

Preferably the CBD is in the form of a highly purified extract of cannabis which comprises at least 98% (w/w) CBD which comprises less than 0.15% THC and up to 1% CBDV. Alternatively, the CBD is present as a synthetic compound.

Preferably the dose of CBD is below 50 mg/kg/day. More preferably the dose of CBD is greater than 20 mg/kg/day.

Preferably the childhood-onset epilepsy is: Lennox-Gastaut Syndrome; Myoclonic Absence Epilepsy; Tuberous Sclerosis Complex; Dravet Syndrome; Doose Syndrome; Jeavons Syndrome; CDKL5; Dup15q; Neuronal ceroid lipofuscinoses (NCL) and brain abnormalities.

In accordance with a second aspect of the present invention there is provided a method of treating childhood-onset epilepsy in an individual in need thereof, comprising administering to the patient a therapeutically effective amount of cannabidiol with caution, wherein the individual is taking an immunosuppressant drug concurrently.

Preferably the said caution comprises lowering the dose of cannabidiol. Alternatively the said caution comprises lowering the dose of the immunosuppressant drug.

Preferably the immunosuppressant drug is tacrolimus.

Preferably the said caution comprises monitoring said individual for side effects.

More preferably the said caution further comprises discontinuing cannabidiol if said side effects are observed.

More preferably still the said caution comprises advising said individual of side effects from said concurrent therapy.

Preferably the individual is a human.

Definitions

Definitions of some of the terms used to describe the invention are detailed below:

The cannabinoids described in the present application are listed below along with their standard abbreviations.

TABLE 4

| Cannabinoids and their abbreviations | | |
|---|---|---|
| CBD | Cannabidiol | |
| CBDA | Cannabidiolic acid | |
| CBDV | Cannabidivarin | |
| CBDVA | Cannabidivarinic acid | |
| THC | Tetrahydrocannabinol | |

The table above is not exhaustive and merely details the cannabinoids which are identified in the present application for reference. So far over 60 different cannabinoids have been identified and these cannabinoids can be split into different groups as follows: Phytocannabinoids; Endocannabinoids and Synthetic cannabinoids (which may be novel cannabinoids or synthetically produced phytocannabinoids or endocannabinoids).

"Phytocannabinoids" are cannabinoids that originate from nature and can be found in the cannabis plant. The phytocannabinoids can be isolated from plants to produce a highly purified extract or can be reproduced synthetically.

"Highly purified cannabinoid extracts" are defined as cannabinoids that have been extracted from the cannabis plant and purified to the extent that other cannabinoids and non-cannabinoid components that are co-extracted with the cannabinoids have been substantially removed, such that the highly purified cannabinoid is greater than or equal to 98% (w/w) pure.

"Synthetic cannabinoids" are compounds that have a cannabinoid or cannabinoid-like structure and are manufactured using chemical means rather than by the plant.

Phytocannabinoids can be obtained as either the neutral (decarboxylated form) or the carboxylic acid form depending on the method used to extract the cannabinoids. For example, it is known that heating the carboxylic acid form will cause most of the carboxylic acid form to decarboxylate into the neutral form.

"Treatment-resistant epilepsy" (TRE) or "intractable epilepsy" is defined as per the ILAE guidance of 2009 as epilepsy that is not adequately controlled by trials of one or more AED.

"Childhood epilepsy" refers to the many different syndromes and genetic mutations that can occur to cause epilepsy in childhood. Examples of some of these are as follows: Dravet Syndrome; Myoclonic-Absence Epilepsy; Lennox-Gastaut syndrome; Generalized Epilepsy of unknown origin; CDKL5 mutation; Aicardi syndrome; tuberous sclerosis complex; bilateral polymicrogyria; Dup15q; SNAP25; and febrile infection related epilepsy syndrome (FIRES); benign rolandic epilepsy; juvenile myoclonic epilepsy; infantile spasm (West syndrome); and Landau-Kleffner syndrome. The list above is non-exhaustive as many different childhood epilepsies exist.

BRIEF DESCRIPTION OF THE DRAWINGS

Embodiments of the invention are further described hereinafter with reference to the accompanying drawings, in which.

DETAILED DESCRIPTION

Preparation of Highly Purified CBD Extract

The following describes the production of the highly-purified (>98% w/w) cannabidiol extract which has a known and constant composition was used in the Examples below.

In summary the drug substance used is a liquid carbon dioxide extract of high-CBD containing chemotypes of *Cannabis sativa* L. which had been further purified by a solvent crystallization method to yield CBD. The crystallisation process specifically removes other cannabinoids and plant components to yield greater than 98% CBD. Although the CBD is highly purified because it is produced from a cannabis plant rather than synthetically there is a small number of other cannabinoids which are co-produced and co-extracted with the CBD. Details of these cannabinoids and the quantities in which they are present in the medication are as described in Table 5 below.

TABLE 5

| Composition of highly purified CBD extract | |
|---|---|
| Cannabinoid | Concentration |
| CBD | >98% w/w |
| CBDA | NMT 0.15% w/w |
| CBDV | NMT 1.0% w/w |
| $\Delta^9$ THC | NMT 0.15% w/w |
| CBD-04 | NMT 0.5% w/w |

>—greater than
NMT—not more than

Example 1: Drug-Drug Interaction Between Cannabidiol (CBD) and Immunosuppressants The patient was a 33 year old female with refractory epilepsy receiving the immunosuppressant drug tacrolimus for interstitial nephritis.

The patient had been stable on tacrolimus at a dose of 5 mg twice per day for a year prior to entry into a clinical trial on the use of CBD to treat childhood-onset epilepsy. At the time of entry into the study her blood level of tacrolimus was between 3.9 and 8.4 ng/mL. She also had a baseline Serum Creatine level of 1.16 mg/dL.

The patient was initially randomized to the sesame oil placebo arm of the trial, during this phase there was no change in the levels of tacrolimus or serum creatine.

However, when the patient entered into the open label phase of the study and began receiving CBD she showed signs of tacrolimus toxicity with a serum creatine level of 2.4 mg/dL.

Figure 1:
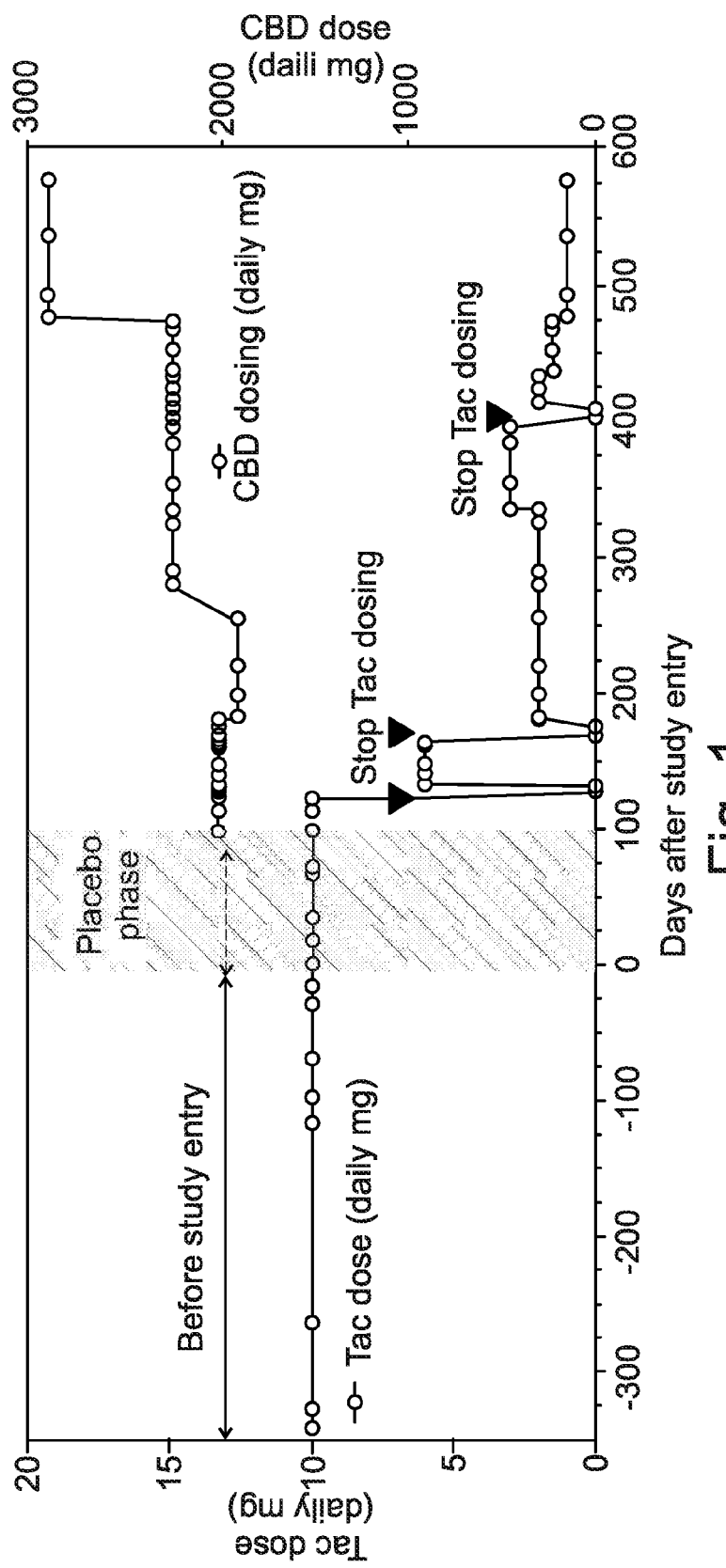
FIG. 1 shows the Daily doses of Tacrolimus (Tac) and Cannabidiol (CBD) during study period.
Figure 2:
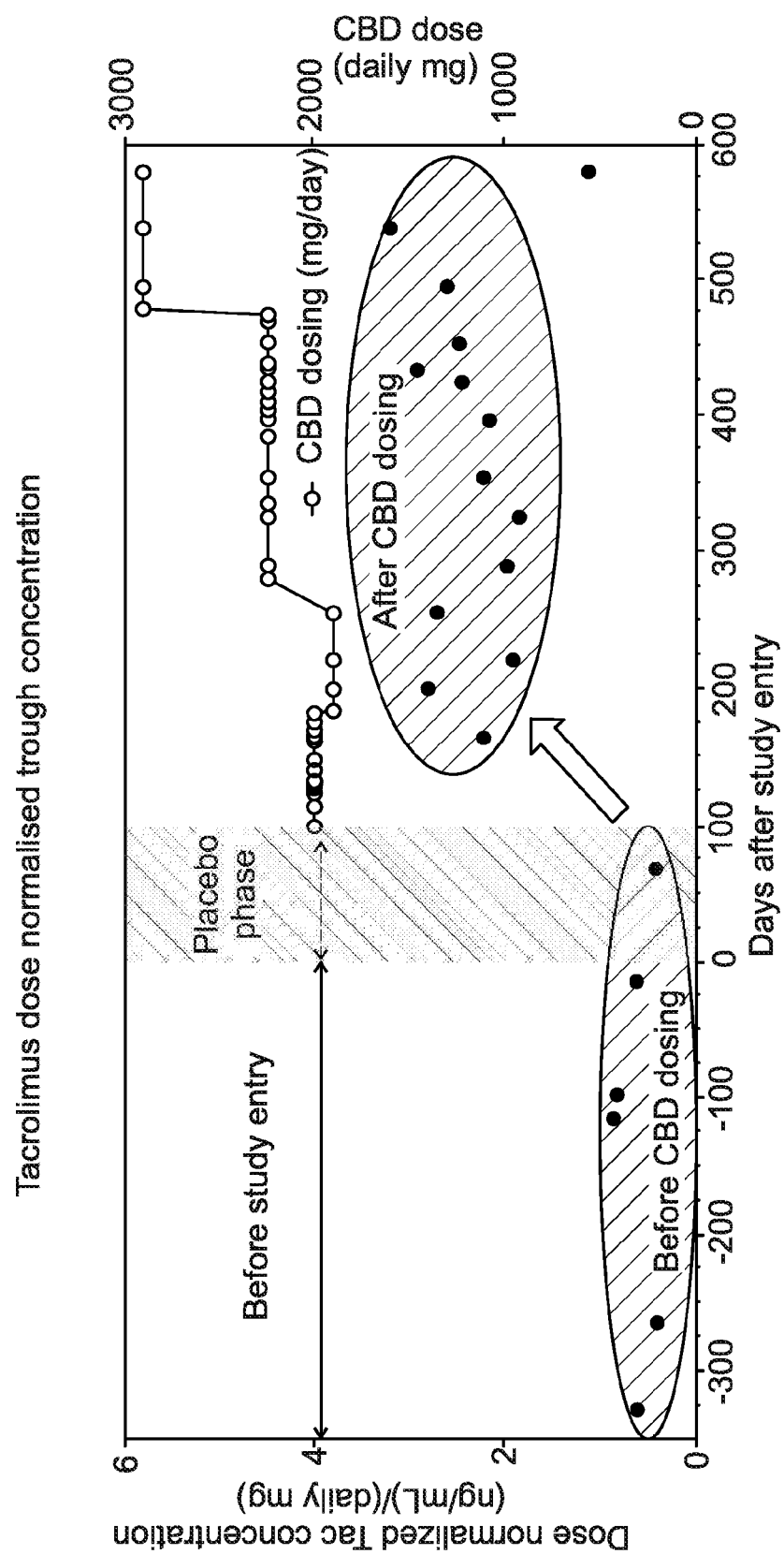
FIG. 2 shows the Tacrolimus dose normalised trough concentration.

The dose of tacrolimus was reduced repeatedly while receiving CBD as described in FIG. 1. A dose of 0.5 mg twice per day (a 10-fold reduction) was finally reached. At this dose the tacrolimus concentrations were normalised as shown in FIG. 2.

Such a finding delineates an important concern for the transplant community with the increasing legalization of marijuana. This drug-drug interaction may have implications in solid organ transplant recipients which are not correctly monitored over the course of their treatment.

CONCLUSIONS

Patients that are taking immunosuppressant drugs such as tacrolimus should be carefully monitored over the course of their treatment with CBD to ensure toxicity does not occur.

The invention claimed is:

1. A method of treating childhood-onset epilepsy in a patient who is concurrently taking tacrolimus, comprising:
   administering to the patient a drug substance comprising at least 98% (w/w) cannabidiol (CBD) and less than 0.15% (w/w) THC;
   detecting toxic blood levels of tacrolimus or one or more associated markers; and
   reducing the dose of tacrolimus to no more than 5 mg per day.

2. The method according to claim 1, wherein the dose of CBD is lowered.

3. The method according to claim 1, wherein the drug substance is in the form of a highly purified extract of cannabis which comprises at least 98% (w/w) CBD.

4. The method according to claim 1, wherein the CBD is present as a synthetic compound.

5. The method according to claim 3, wherein the extract further comprises up to 1% (w/w) CBDV.

6. The method according to claim 1, wherein the dose of CBD is below 50 mg/kg/day.

7. The method according to claim 1, wherein the dose of CBD is greater than 20 mg/kg/day.

8. The method according to claim 1, wherein the childhood-onset epilepsy is: Lennox-Gastaut Syndrome; Myoclonic Absence Epilepsy; Tuberous Sclerosis Complex; Dravet Syndrome; Doose Syndrome; Jeavons Syndrome; CDKL5; Dup15q; Neuronal ceroid lipofuscinoses (NCL) or brain abnormalities.

9. The method of claim 1, wherein the associated markers comprise serum creatine.

10. The method of claim 9, wherein the serum creatine become toxic when the blood levels are 2.4 mg/dL or more.

11. The method of claim 1, wherein the dose of tacrolimus is reduced by up to 10-fold.

12. The method of claim 1, wherein the dose of tacrolimus is reduced to 0.5 mg twice per day.

\* \* \* \* \*